(12) United States Patent
Pouton et al.

(10) Patent No.: US 11,446,393 B2
(45) Date of Patent: Sep. 20, 2022

(54) NON-VIRAL GENE DELIVERY AGENT COMPRISING LIPOPEPTIDE (LP) COMPOUNDS

(71) Applicant: MONASH UNIVERSITY, Clayton (AU)

(72) Inventors: Colin William Pouton, Alphington (AU); Kha Tu Joan Ho, Sunshine North (AU); Paul James White, Strathmore Heights (AU); Catherine Thoa Bui, Footscray (AU); Nabila Akhtar, Moonee Ponds (AU); Hareth Ali Al-Wassiti, Brunswick (AU)

(73) Assignee: Monash University, Victoria (AU)

( * ) Notice: Subject to any disclaimer, the term of this patent is extended or adjusted under 35 U.S.C. 154(b) by 20 days.

(21) Appl. No.: 16/622,136

(22) PCT Filed: Jun. 8, 2018

(86) PCT No.: PCT/AU2018/000093
§ 371 (c)(1),
(2) Date: Dec. 12, 2019

(87) PCT Pub. No.: WO2018/227231
PCT Pub. Date: Dec. 20, 2018

(65) Prior Publication Data
US 2020/0246487 A1 Aug. 6, 2020

(30) Foreign Application Priority Data
Jun. 13, 2017 (AU) ............................... 2017902238

(51) Int. Cl.
*A61K 48/00* (2006.01)
*A61K 9/00* (2006.01)
*A61K 9/14* (2006.01)
*C12N 15/88* (2006.01)

(52) U.S. Cl.
CPC ........ *A61K 48/0025* (2013.01); *A61K 9/0019* (2013.01); *A61K 9/145* (2013.01); *A61K 9/146* (2013.01); *C12N 15/88* (2013.01)

(58) Field of Classification Search
CPC .. A61K 48/0025; A61K 9/0019; A61K 9/145; A61K 9/146; C12N 15/88
See application file for complete search history.

(56) References Cited

U.S. PATENT DOCUMENTS

2011/0268653 A1    11/2011   Negrette et al.

FOREIGN PATENT DOCUMENTS

| WO | WO 1996/041606 | 12/1996 |
| WO | WO 2009/046220 | 4/2009 |

OTHER PUBLICATIONS

Dong et al., "Lipopeptide nanoparticles for potent and selective siRNA delivery in rodents and nonhuman primates", Proceedings of the National Academy of Sciences, Mar. 18, 2014, vol. 111(11), pp. 3955-3960.
Extended European Search Report for European Patent Application No. 18816853.8, dated Jan. 29, 2021, 8 pages.
Bruun et al. "Investigation of enzyme-sensitive lipid nanoparticles for delivery of siRNA to blood-brain barrier and glioma cells," International Journal of Nanomedicine, Sep. 2015, vol. 10, pp. 5995-6008.
Du et al. "Biodegradable nanoparticles of mPEG-PLGA-PLL triblock copolymers as novel non-viral vectors for improving siRNA delivery and gene silencing," International Journal of Molecular Sciences, 2012, vol. 13, No. 1, pp. 516-533.
Ewert et al. "Synthesis of linear and cyclic peptide-PEG-lipids for stabilization and targeting of cationic liposome-DNA complexes," Bioorganic & Medicinal Chemistry Letters, Mar. 2016, vol. 26, No. 6, pp. 1618-1623.
Gjetting et al. "Effective nanoparticle-based gene delivery by a protease triggered charge switch," Advanced Healthcare Materials, Jul. 2014, vol. 3, No. 7, pp. 1107-1118.
Ho et al. "Tissue-specific Calibration of Real-time PCR Facilitates Absolute Quantification of Plasmid DNA in Biodistribution Studies," Molecular Therapy-Nucleic Acids, 2016, vol. 5, e371, 9 pages.
Jeffs et al. "A Scalable, Extrusion-Free Method for Efficient Liposomal Encapsulation of Plasmid DNA," Pharmaceutical Research, Mar. 2005, vol. 22, No. 3, pp. 362-372.
Johnson et al. "HPMA-oligolysine copolymers for gene delivery: optimization of peptide length and polymer molecular weight," Journal of Controlled Release, Oct. 2011, vol. 155, No. 2, pp. 303-311.
Majumder et al. "Inhibiting tumor growth by targeting liposomally encapsulated CDC20siRNA to tumor vasculature: therapeutic RNA interference," Journal of Controlled Release, Apr. 2014, vol. 180, pp. 100-108.
Suk et al. "PEGylation as a strategy for improving nanoparticle-based drug and gene delivery," Advanced Drug Delivery Reviews, Apr. 2016, vol. 99, Part A, pp. 28-51.
Tarwadi et al. "Preparation and in vitro evaluation of novel lipopeptide transfection agents for efficient gene delivery," Bioconjugate Chemistry, Apr. 2008, vol. 19, No. 4, pp. 940-950.
Wang et al. "Targeting the urokinase plasminogen activator receptor with synthetic self-assembly nanoparticles," Bioconjugate Chemistry, Jan. 2009, vol. 20, No. 1, pp. 32-40.
International Search Report and Written Opinion for International (PCT) Patent Application No. PCT/AU2018/000093, dated Aug. 29, 2018, 14 pages.

(Continued)

*Primary Examiner* — Robert S Cabral
(74) *Attorney, Agent, or Firm* — Sheridan Ross P.C.

(57) ABSTRACT

Non-viral nucleic acid delivery agents and methods for the delivery or transfer of nucleic acid molecules to target cells are disclosed. The agents comprise a complex of a nucleic acid cargo for delivery, one or more lipopeptide compound, and one or more polymeric charge-neutralising agent, and the complex is in the form of a particle with substantially neutral or negative surface charge. The agents and methods may be useful in a variety of applications such as therapies (including gene therapies and nucleic acid vaccinations) for diseases and medical disorders.

22 Claims, 8 Drawing Sheets

Specification includes a Sequence Listing.

(56) References Cited

OTHER PUBLICATIONS

International Preliminary Report on Patentability for International (PCT) Patent Application No. PCT/AU2018/000093, dated May 3, 2019, 28 pages.

A

B

A

B

A

B (A)

(B)

SEQUENCE LISTING

```
<160> NUMBER OF SEQ ID NOS: 14

<210> SEQ ID NO 1
<211> LENGTH: 6
<212> TYPE: PRT
<213> ORGANISM: Artificial Sequence
<220> FEATURE:
<223> OTHER INFORMATION: Lipopeptide

<400> SEQUENCE: 1

Cys His His Lys Lys Lys
1               5

<210> SEQ ID NO 2
<211> LENGTH: 6
<212> TYPE: PRT
<213> ORGANISM: Artificial Sequence
<220> FEATURE:
<223> OTHER INFORMATION: Hexapeptide
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (3)..(3)
<223> OTHER INFORMATION: Xaa is any amino acid

<400> SEQUENCE: 2

Cys Xaa Xaa Lys Lys Lys
1               5

<210> SEQ ID NO 3
<211> LENGTH: 6
<212> TYPE: PRT
<213> ORGANISM: Artificial Sequence
<220> FEATURE:
<223> OTHER INFORMATION: Hexapeptide
<220> FEATURE:
<221> NAME/KEY: VARIANT
<222> LOCATION: (1)..(1)
<223> OTHER INFORMATION: Xaa is any amino acid other than Cys
<220> FEATURE:
<221> NAME/KEY: VARIANT
<222> LOCATION: (2)..(2)
<223> OTHER INFORMATION: Xaa is any amino acid other than Cys
<220> FEATURE:
<221> NAME/KEY: VARIANT
<222> LOCATION: (3)..(3)
<223> OTHER INFORMATION: Xaa is any amino acid other than Cys

<400> SEQUENCE: 3

Xaa Xaa Xaa Lys Lys Lys
1               5

<210> SEQ ID NO 4
<211> LENGTH: 6
<212> TYPE: PRT
<213> ORGANISM: Artificial Sequence
<220> FEATURE:
<223> OTHER INFORMATION: Lipopeptide
```

```
<220> FEATURE:
<221> NAME/KEY: VARIANT
<222> LOCATION: (2)..(2)
<223> OTHER INFORMATION: Xaa is any amino acid other than Cys
<220> FEATURE:
<221> NAME/KEY: VARIANT
<222> LOCATION: (3)..(3)
<223> OTHER INFORMATION: Xaa is any amino acid other than Cys

<400> SEQUENCE: 4

Ser Xaa Xaa Lys Lys Lys
1               5

<210> SEQ ID NO 5
<211> LENGTH: 6
<212> TYPE: PRT
<213> ORGANISM: Artificial Sequence
<220> FEATURE:
<223> OTHER INFORMATION: Lipopeptide

<400> SEQUENCE: 5

Cys Ala Ala Lys Lys Lys
1               5

<210> SEQ ID NO 6
<211> LENGTH: 6
<212> TYPE: PRT
<213> ORGANISM: Artificial Sequence
<220> FEATURE:
<223> OTHER INFORMATION: Lipopeptide

<400> SEQUENCE: 6

Cys His His Arg Arg Arg
1               5

<210> SEQ ID NO 7
<211> LENGTH: 6
<212> TYPE: PRT
<213> ORGANISM: Artificial Sequence
<220> FEATURE:
<223> OTHER INFORMATION: Lipopeptide

<400> SEQUENCE: 7

Ser His His Lys Lys Lys
1               5

<210> SEQ ID NO 8
<211> LENGTH: 6
<212> TYPE: PRT
<213> ORGANISM: Artificial Sequence
<220> FEATURE:
<223> OTHER INFORMATION: Lipopeptide

<400> SEQUENCE: 8

Ser Ala Ala Lys Lys Lys
1               5

<210> SEQ ID NO 9
<211> LENGTH: 6
<212> TYPE: PRT
<213> ORGANISM: Artificial Sequence
<220> FEATURE:
<223> OTHER INFORMATION: Lipopeptide

<400> SEQUENCE: 9

Ser His His Arg Arg Arg
1               5
```

```
<210> SEQ ID NO 10
<211> LENGTH: 8
<212> TYPE: PRT
<213> ORGANISM: Artificial Sequence
<220> FEATURE:
<223> OTHER INFORMATION: OVA257-264 synthetic peptide

<400> SEQUENCE: 10

Ser Ile Ile Asn Phe Glu Lys Leu
1               5

<210> SEQ ID NO 11
<211> LENGTH: 20
<212> TYPE: DNA
<213> ORGANISM: Artificial Sequence
<220> FEATURE:
<223> OTHER INFORMATION: Primer to amplify a fragment of pCMVluc

<400> SEQUENCE: 11
cctcataaag gccaagaagg                                              20

<210> SEQ ID NO 12
<211> LENGTH: 19
<212> TYPE: DNA
<213> ORGANISM: Artificial Sequence
<220> FEATURE:
<223> OTHER INFORMATION: Primer to amplify a fragment of pCMVluc

<400> SEQUENCE: 12
acaccggcct tattccaag                                               19

<210> SEQ ID NO 13
<211> LENGTH: 6
<212> TYPE: PRT
<213> ORGANISM: Artificial Sequence
<220> FEATURE:
<223> OTHER INFORMATION: Lipopeptide

<400> SEQUENCE: 13

Cys Lys Lys Lys Lys Lys
1               5

<210> SEQ ID NO 14
<211> LENGTH: 5
<212> TYPE: PRT
<213> ORGANISM: Artificial sequence
<220> FEATURE:
<223> OTHER INFORMATION: Pentapeptide
<220> FEATURE:
<221> NAME/KEY: VARIANT
<222> LOCATION: (1)..(1)
<223> OTHER INFORMATION: Xaa is any amino acid other than Cys
<220> FEATURE:
<221> NAME/KEY: VARIANT
<222> LOCATION: (2)..(2)
<223> OTHER INFORMATION: Xaa is any amino acid other than Cys

<400> SEQUENCE: 14

Xaa Xaa Lys Lys Lys
1               5
```

NON-VIRAL GENE DELIVERY AGENT COMPRISING LIPOPEPTIDE (LP) COMPOUNDS

TECHNICAL FIELD

The present disclosure relates to agents and methods for the delivery or transfer of nucleic acid molecules to target cells for applications such as therapies (including gene therapies and nucleic acid vaccinations) for diseases and medical disorders.

CROSS-REFERENCE TO RELATED APPLICATIONS

This application is a national stage application under 35 U.S.C. 371 and claims the benefit of PCT Application No. PCT/AU2018/000093 having an international filing date of 8 Jun. 2018, which designated the United States, which PCT application claimed the benefit of Australian Provisional Patent Application No 2017902238 titled "Novel gene delivery systems 2" filed on 13 Jun. 2017, the contents of each of which are hereby incorporated by reference in their entireties.

REFERENCE TO SEQUENCE LISTING

This application contains a Sequence Listing submitted as an electronic text file named "Sequence_Listing_file.TXT", having a size in bytes of 4,000 bytes, and created on 8 Jun. 2018. The information contained in this electronic file is hereby incorporated by reference in its entirety pursuant to 37 CFR § 1.52(e)(5).

BACKGROUND

The delivery or transfer of useful nucleic acids (eg oligonucleotides and polynucleotides) to target cells using non-viral vectors and agents is highly desirable for a number of reasons including the potential of improved safety (ie relative to viral vectors such as retroviral vectors that may lack the regulatory mechanisms required to safely express a therapeutic gene without interfering with innate genomic activities [1]), stability and suitability for production as "bulk" pharmaceuticals. Amongst the strategies tried for non-viral nucleic acid transfer is the very simple technique of systemic administration of a large volume of plasmid DNA solution (which has been found to result in high pressure in blood vessels and extravasations of plasmids); microinjection of plasmids (eg large artificial chromosomes) directly into cells which can result in the stable fusing of the plasmids with host genomic DNA; and electroporation, a popular and useful way to transfect cells for in vitro studies, which has also been engineered for in vivo animal models. However, all of these have limited practicality for use in human trials.

Lipofection, the complexation of nucleic acids and cationic lipids to form cationic particles known as lipid nanoparticles (LNP), has served as the basis of another non-viral gene transfer tool. However, like the strategies mentioned above, its usefulness has mainly been limited to cell culture and some simple animal models, mainly due to low efficiency and consequent toxicity of effective high doses [2]. Nevertheless, several clinical trials have been approved making use of lipid-nucleic acid nanoparticle complexes, and various studies have attempted to change the characteristics of the complexes to reduce toxicity and achieve more tissue-specificity; for example, by coating the exterior of the complexes with electrostatically adsorbed, poly(glutamic acid)-based peptide coatings has resulted in reduced toxicity compared to naked DNA-complexes in vivo [3]. In other modifications, polyethylene glycol (PEG) has been used to "shield" or neutralise the positive charges of the cationic particles which promote electronic association with negatively charged serum proteins, along with subsequent opsonisation and clearance of the particles [4]. For example, in some cases, LNPs have been produced by complexation of nucleic acids with cationic lipids as well as "PEGylated" lipids such as phosphatidylethanolamine-PEG (PE-PEG)[5] in order to improve biodistribution and efficiency. However, despite significant progress in the development of LNPs for potential therapeutic use, a number of doubts remain including concerns that the cationic lipids used (which are usually phospholipid derivatives) may not be well tolerated in the body, particularly over longer periods (eg for long term or chronic use of a LNP-based therapeutic agent) due to innate immune activation [6], low degradation and/or clearance.

Accordingly, there is an on-going need to identify and develop improved and/or alternative agents and methods for the delivery or transfer of useful nucleic acid molecules (such as therapeutic nucleic acids) to target cells. To this end, the present Applicant looked to the alternative strategy of using cationic lipopeptides (LPs) instead of cationic lipids.

As the name suggests, lipopeptides comprise a peptide conjugated to a hydrophobic moiety (eg a lipid). For use as a condensing agent, the LPs are cationic and, as such, typically the peptide component will include amino acids such as lysine and arginine, which due to their strongly basic/positively charged properties, allow for the condensation of nucleic acid molecules such as plasmid DNA at physiological pH [7]. In addition, the peptide may include histidine residues, which are also believed to increase transfection efficiency by promoting endosomal escape of the nucleic acid [8], and/or cysteine residues which can allow for the formation of disulphide bonds between peptide molecules, thereby enhancing the stability of the lipopeptide-nucleic acid complex by preventing dissociation of the nucleic acid and the lipopeptide in solution [9]. The hydrophobic moiety of the lipopeptide is also believed to assist in the stabilisation of the nucleic acid-lipopeptide complex. Typical moieties include lipophilic chains (eg stearoyl and cholesteryl) or non-polar residue repeats (eg valines)[10, 11].

Hereinafter, the present Applicant discloses the further development of LPs for use in nucleic acid delivery agents, such as the self-cross linking cationic LP, stearoyl-Cys-His-His-Lys-Lys-Lys (also referred to hereinafter as stearoyl-$CH_2K_3$ LP; SEQ ID NO: 1). Such LPs may offer advantages in terms of ease of manufacture as they can readily self-assemble with nucleic acid molecules such as plasmid DNA in aqueous solution, circumventing the need for organic-based solvent preparations (ie as required for the preparation of LNPs), and thereby limiting the chance of carry-over of the unwanted solvent. Moreover, as LPs such as stearoyl-Cys-His-His-Lys-Lys-Lys are comprised of biocompatible moieties, it is anticipated that nucleic acid delivery agents incorporating LPs may show lower or at least acceptable toxicity than alternative nucleic acid delivery agents such as LNPs.

SUMMARY

According to a first aspect, this disclosure provides a non-viral nucleic acid delivery agent comprising a complex of:

(i) a nucleic acid cargo for delivery to a cell;
(ii) one or more lipopeptide compound; and
(iii) one or more polymeric charge-neutralising agent;
wherein said complex is in the form of a particle with substantially neutral or negative surface charge.

In one particular embodiment, the non-viral nucleic acid delivery agent of the present disclosure may be regarded as a DNA or RNA vaccine.

In a second aspect, the present disclosure provides a method of delivering a nucleic acid molecule to a cell of a subject, said method comprising the steps of:
providing a non-viral nucleic acid delivery agent according to the first aspect; and
delivering the non-viral nucleic acid delivery agent to said cell of the subject.

The non-viral nucleic acid delivery agent may be delivered to the cell using a simple needle injection (eg for parenteral administration such as intramuscular (im) administration).

In a third aspect, the present disclosure provides a pharmaceutical composition comprising a non-viral delivery nucleic acid agent according to the first aspect in combination with a pharmaceutically acceptable carrier or excipient.

In a fourth aspect, the present disclosure provides a method of producing a non-viral delivery nucleic acid agent according to the first aspect, said method comprising:
combining a nucleic acid cargo, one or more lipopeptide compound, and one or more polymeric charge-neutralising agent under conditions suitable for the formation of complexed particles.

DETAILED DESCRIPTION

Figure 1:
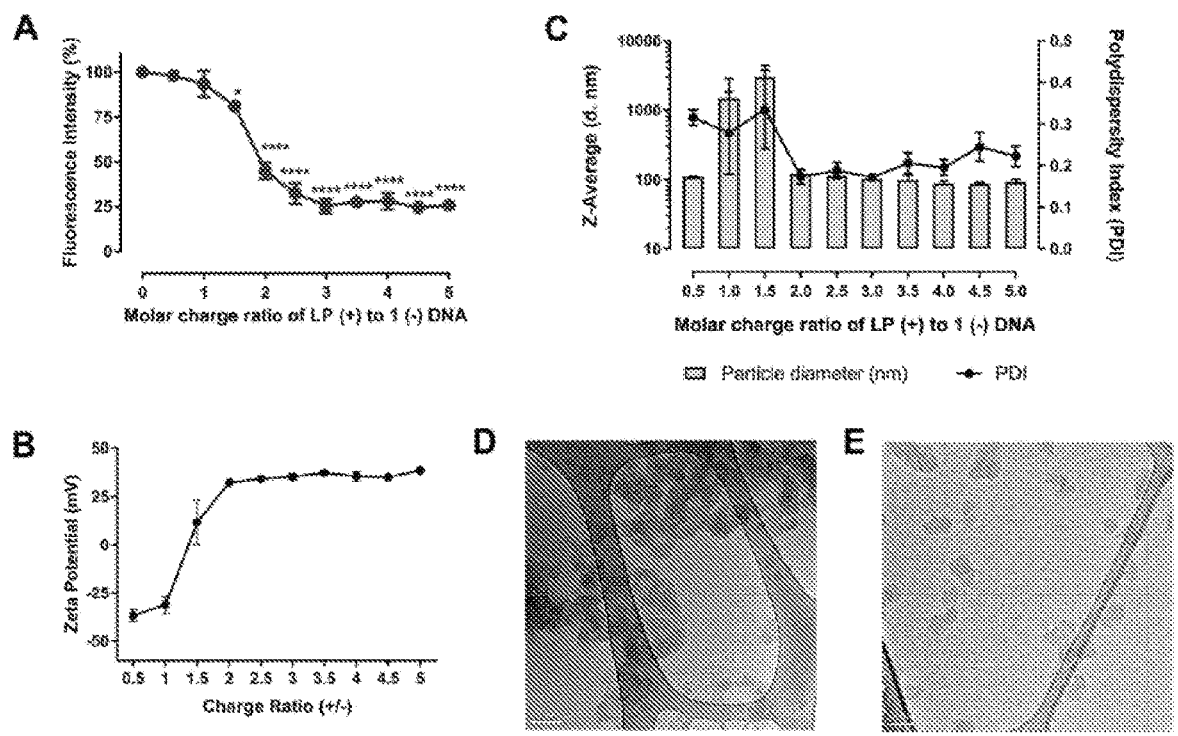
FIG. 1 provides results of characterisation studies of LNPs (using the example of LP/DNA complexes). A) Dye exclusion profile of LP/DNA complexes prepared with stearoyl-$CH_2K_3$. All data points are calculated as the percentage fluorescence intensity of plasmid DNA in solution. *$p<0.05$ and ****$p<0.0001$ for significant differences in fluorescence intensity when compared to DNA alone (One-way ANOVA, Dunnett's post hoc test). B) Zeta potential and C) mean particle size and polydispersity index of stearoyl-$CH_2K_3$/DNA complexes over a range of charge ratio. As the (+/−) charge ratio of LP to DNA increased, the zeta potential increased, whilst the Z-average remained low (generally between 10-100 nm), with the exception of complexes formed at charge ratios close to unity. All data is presented as mean±SEM of n=3 separate experiments. Cryo-TEM images of the LP/DNA complexes prepared at a charge ratio of D) 1.5:1 and E) 2.5:1 illustrating aggregate complexes and smaller ~30 nm particles, respectively. Scale bars are in the left-hand bottom corner (in D=100 nm, in E=50 nm)

In a first aspect, this disclosure provides a non-viral nucleic acid delivery agent comprising a complex of:

(i) a nucleic acid cargo for delivery to a cell;
(ii) one or more lipopeptide compound; and
(iii) one or more polymeric charge-neutralising agent;
wherein said complex is in the form of a particle with substantially neutral or negative surface charge.

As used herein, the term "non-viral nucleic acid delivery agent" is to be understood as referring to agents that may be employed in non-viral gene delivery methods such as well known physical approaches (such as needle injection, gene gun, electroporation, ultrasound and hydrodynamic delivery) and/or chemical approaches (such as the use of synthetic or naturally occurring compounds as carriers to deliver a nucleic acid to a cell). As such, the term does not refer to viral-based gene delivery agents such as viral vectors. The non-viral nucleic acid delivery agent according to the present disclosure is provided in a particle form, preferably as a fine particle or nanoparticle with an average particle diameter size in the range of 50 nm to 300 nm, more preferably 50 nm to 150 nm, and most preferably within the range of 50 nm to 125 nm.

The non-viral nucleic acid delivery agent may be useful for, for example, gene delivery or transfer for laboratory (eg research) or medical/veterinary applications, including nucleic acid vaccinations and gene therapy for diseases and medical disorders.

The nucleic acid cargo may comprise a nucleic acid molecule. The term "nucleic acid molecule" as used herein includes any single- or double-stranded polyribonucleotide or polydeoxribonucleotide. As such, the term includes single- and double-stranded DNA (eg cDNA and genomic DNA, and DNA in a linear form or a non-linear (ie circularised) form (eg a DNA plasmid)), DNA that is a mixture of single- and double-stranded regions, single- and double-stranded RNA (eg messenger RNA (mRNA)), and RNA that is a mixture of single- and double-stranded regions, and hybrid molecules comprising DNA and RNA that may be single-stranded or, more typically, double-stranded or a mixture of single- and double-stranded regions. In addition, the term "nucleic acid molecule" also includes DNA and RNA containing one or more modified bases and DNA and RNA with backbones modified for stability or for other reasons. "Modified" bases include, for example, tritylated bases, unusual bases such as inosine, and methylated bases such as 5-methyl cytosine and N1-methyl pseudouracil; mRNA that has been chemically modified in this way is sometimes referred to as "modified mRNA" or "modRNA". The term "nucleic acid molecule" also embraces relatively short polynucleotides, often referred to as oligonucleotides.

The nucleic acid cargo may comprise a nucleic acid molecule which encodes a functional gene or might otherwise comprise a nucleic acid molecule which encodes, for example, a non-functional gene or part thereof, or another entity that is capable of effecting an alteration in the function of a cell (eg an increase or decrease in the production of a protein) such as, for example, a nucleic acid molecule which encodes interfering RNA (iRNA) or constitutes an inhibitory RNA molecule itself, or which provides a cis acting gene regulatory element. Where the nucleic acid cargo comprises a nucleic acid molecule which provides a functional gene (ie a transgene or gene-of-interest), the gene may consist in an expression cassette comprising a suitable promoter sequence (eg a constitutive or inducible promoter) operably linked to a nucleotide sequence encoding a protein(s), oligopeptide(s) or peptide(s) of interest such as, for example, an antigen or epitope(s) that may be of vaccine significance, or an enzyme, receptor or hormone which may be lacking or defective in a disease or medical disorder so as to provide the basis for a gene therapy agent. For example, in the context of a nucleic acid vaccination, the nucleic acid cargo may comprise a DNA molecule encoding one or more of the hepatitis B virus (HBV) surface, envelope and core antigens (commonly denoted as HBsAg, HbeAg and HbcAg respectively) to provide a vaccine against HBV. In another example, in the context of a treatment of a disease or medical condition, the nucleic acid cargo may comprise a DNA molecule encoding the hypoxanthine phosphoribosyl transferase (HPRT) protein for treatment of Lesch-Nyhan syndrome. Similarly, the nucleic acid cargo may be a messenger RNA encoding a protein(s), oligopeptide(s) or peptide(s) of interest such as, for example, an antigen or epitope(s) which may be of vaccine significance, or an enzyme, receptor or hormone which may be lacking or defective in a disease or medical disorder so as to provide the basis for a therapy for the particular disease or medical condition. As would be readily understood by those skilled in the art, such mRNA is provided with the required sequence elements to enable the mRNA to be efficiently translated within the cytoplasm of the cell. Preferably, such mRNA will also include modified bases such as 5-methyl cytosine and N1-methyl pseudouracil as these may confer a number of advantages such as stability, reduced immune stimulatory activity and enhanced translation efficiency [12]. In other embodiments, the nucleic acid cargo may be a self-amplifying replicon RNA (such as those derived from the alphavirus, a group of (+)ssRNA viruses [17]) comprising a transgene, which generates, within the cytoplasm of the cell, mRNA from the transgene for translation into a protein(s), oligopeptide(s) or peptide(s) of interest such as, for example, an antigen or epitope(s), or an enzyme, receptor or hormone.

The size of the nucleic acid molecule comprising the nucleic acid cargo may be in the range of 5 bases to 50 kilobases in length. For example, where the nucleic acid molecule is an oligonucleotide molecule (including peptide-nucleic acids and phosphothioate-modified nucleic acids), the nucleic acid molecule may be in the range of 5 to 50 bases in length, whereas for a nucleic acid molecule that is a polynucleotide molecule, the nucleic acid molecule may be in the range of 50 bases to 50 kilobases in length, more preferably, 1 to 10 kilobases in length.

The non-viral nucleic acid delivery agent comprises one or more lipopeptide compound. It has been found that suitable lipopeptides may complex with a nucleic acid cargo and a polymeric charge-neutralising agent to form particles with substantially neutral or negative surface charge. Such lipopeptides may act as a nucleic acid condensing agent and can be used in place of cationic lipids as found in LNPs. Accordingly, in some preferred embodiments, the non-viral nucleic acid delivery agent has no cationic lipids present. It is also preferred that the non-viral nucleic acid delivery agent is free of polycationic ligands such as poly-L-Lysine (PLL) and polyethylenimine (PEI).

Suitable lipopeptides include those of the general formula I:

$$\text{R-L-peptide} \tag{I}$$

wherein R is a linear or branched alkyl (eg $C_{12\text{-}35}$, but more preferably $C_{12\text{-}25}$) such as $CH_3\text{---}(CH_2)_n\text{---}$, where n is an integer in the range of 11 to 21 (preferably 13 to 18);

L is a linker group (eg any suitable linking group such as chemical linkers including, for example, polyethylene glycol (PEG)-based linkers and disulphide (—S—S—) linkers); and the peptide is of any amino acid sequence comprising 2-15 amino acids, preferably 5-10 amino acids, but with the proviso that at least two of the amino acids are independently selected from those with strongly basic/positively charged properties (eg lysine (Lys), arginine (Arg) and histidine (His), and other non-standard ("non-canonical") amino acids such as aza-leucine and N-methyl arginine).

Preferred lipopeptides will typically be of the general formula II:

R—CO-peptide    (II)

wherein

R is $CH_3-(CH_2)_n-$, where n is an integer in the range of 11 to 21, preferably 13 to 18, and the peptide is of any amino acid sequence comprising 2-15 amino acids, preferably 5-10 amino acids, but with the proviso that at least two of the amino acids are independently selected from those with strongly basic/positively charged properties (eg lysine (Lys), arginine (Arg) and histidine (His), and other non-standard ("non-canonical") amino acids such as aza-leucine and N-methyl arginine).

Lipopeptides of the general formula (I) may be produced by, for example, reacting a carboxylic acid derivative of R with the N-terminus of the peptide; hence the notation R—CO-peptide.

In some embodiments, the peptide comprises at least one cysteine (Cys) and at least three residues selected from amino acids with strongly basic/positively charged properties. Preferably, the peptide comprises at least three Lys or Arg amino acids. For example, the peptide may be a 6-mer (ie hexapeptide) comprising the amino acid sequence: Cys-$X^1$-$X^2$-Lys-Lys-Lys (SEQ ID NO: 2), where $X^1$ and $X^2$ are any amino acids and may be the same or different, but wherein $X^1$ and $X^2$ are preferably selected from Arg and His. Accordingly, in some embodiments the lipopeptide may be: stearoyl-Cys-$X^1$-$X^2$-Lys-Lys-Lys (ie where n is 17) (SEQ ID NO: 2). The C-terminus of the peptide component is preferably either free COOH or amide. The Cys residue(s) may enable disulphide cross-linking between lipopeptide molecules to enhance the stability of the formed complexes, and may assist in forming denser particles which may be beneficial in in vitro applications of the non-viral nucleic acid delivery agent. Preferably, the peptide of such embodiments will comprise a single Cys residue which is preferably located at position 1, however other positions within the peptide may also be suitable.

In some other embodiments, the peptide may be free of cysteine (Cys) residues. A lipopeptide devoid of Cys may be advantageous, especially for in vivo applications of the non-viral nucleic acid delivery agent, by simplifying preparation (ie there is no need to ensure that the lipopeptide is reduced before use to form disulphide cross-linking) and, without any disulphide cross-linking of the lipopeptides, in vivo "uncoupling" of the particle complex once delivered to a cell may be more efficient. Like the lipopeptides described in the previous paragraph, the peptide of embodiments wherein the lipopeptide is devoid of Cys will comprise at least three residues selected from amino acids with strongly basic/positively charged properties. Preferably, the peptide comprises at least three Lys or Arg amino acids. For example, the peptide may be a 6-mer comprising the amino acid sequence: $X^0$-$X^1$-$X^2$-Lys-Lys-Lys (SEQ ID NO: 3), where $X^0$ is absent or any amino acid other than Cys (and preferably, Ser or Thr), and $X^1$ and $X^2$ are any amino acids (other than Cys) and may be the same or different, but wherein $X^1$ and $X^2$ are preferably selected from Ala, Arg and His. Accordingly, in some embodiments the lipopeptide may be: stearoyl-Ser-$X^1$-$X^2$-Lys-Lys-Lys (ie where n is 17) (SEQ ID NO: 4). The C-terminus of the peptide component is preferably either free COOH or amide.

In particularly preferred embodiments, the non-viral nucleic acid delivery agent comprises a lipopeptide compound selected from: stearoyl-Cys-His-His-Lys-Lys-Lys (stearoyl-$CH_2K_3$ shown below; SEQ ID NO: 1), stearoyl-Cys-Ala-Ala-Lys-Lys-Lys (stearoyl-$CA_2K_3$; SEQ ID NO: 5) and N-lauryl-Cys-His-His-Arg-Arg-Arg (lauroyl-$CH_2R_3$; SEQ ID NO: 6). The lipopeptides may have free COOH at the C-terminus as shown below or may be provided with amide ($CONH_2$) at the C-terminus.

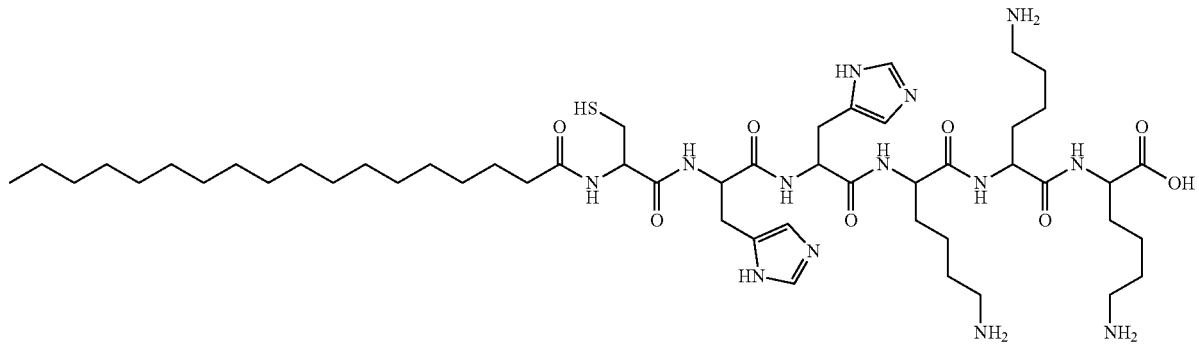

Stearoyl-Cys-His-His-Lys-Lys-Lys

In other particularly preferred embodiments, the non-viral nucleic acid delivery agent comprises a lipopeptide compound selected from: stearoyl-Ser-His-His-Lys-Lys-Lys (stearoyl-$SH_2K_3$ shown below; SEQ ID NO: 7), stearoyl-Ser-Ala-Ala-Lys-Lys-Lys (stearoyl-$SA_2K_3$; SEQ ID NO: 8) and N-lauryl-Ser-His-His-Arg-Arg-Arg (lauroyl-$SH_2R_3$; SEQ ID NO: 9). The lipopeptides may have free COOH at the C-terminus as shown below or may be provided with amide ($CONH_2$) at the C-terminus.

Advantageously, lipopeptides are soluble in water and thereby enable the possible production of the non-viral nucleic acid delivery agent entirely in aqueous media with no requirement for solvents (cf. as required for the preparation of LNPs) or extra purification steps (eg to remove solvents).

The non-viral nucleic acid delivery agent comprises one or more polymeric charge-neutralising agent. It is considered that the polymeric charge-neutralising agent functions so as to shield or neutralise positive charges (ie as may be provided by cationic lipopeptides), such that the particles of the non-viral nucleic acid delivery agent are characterised by a substantially neutral or negative particle surface charge.

Suitable polymeric charge-neutralising agent(s) include derivatives of polyethylene glycol (PEG) incorporating a lipid component such as a phospholipid (eg phosphatidylethanolamine-PEG (PE-PEG) and distearoyl-phosphoethanolamine-(polyethylene glycol) (DSPE-PEG)), poly-amino acid polymers such as polyaspartic acids (PAAs) or polyglutamic acids (PGAs) and other anionic polymers such as poly(acrylic acid) polymers, and certain block copolymers comprising a negatively charged block and a neutral, hydrophilic block (eg block copolymers of poly(acrylic acid) and poly(hydroxypropyl methacrylamide) (polyHPMA), and block copolymers of poly(acrylic acid) and poly(2-hydroxyethyl methacrylamide) (polyHEMA)).

The polymeric charge-neutralising agent(s) preferably shows at least acceptable levels of biocompatibility and/or biodegradability within the body of a subject. Poly-amino acid polymers and, particularly PGAs, show at least acceptable levels of both biocompatibility and biodegradability. Thus, in some preferred embodiments, the polymeric charge-neutralising agent(s) is selected from poly(glutamate)-PEG copolymers (polyGlu-PEG). Particular examples include the block polymers of poly(glutamate) and poly(ethylene glycol); poly(ethylene glycol) is also known as poly(ethylene oxide) or PEG. Such polyGlu-PEG copolymers are commercially available (eg from Alamanda Polymers, Huntsville, Ala., United States of America). In some particular embodiments, the polymeric charge-neutralising agent(s) comprises, for example, a block copolymer comprising 22, 113 or 454 PEG units (mol wt 1000 Da, 5000 Da and 20000 Da, respectively) in combination with 10, 50, 100 or 200 glutamate units (mol wt 1500 Da, 7500 Da, 15000 Da and 30000 Da, respectively). In one particular embodiment, the polymeric charge-neutralising agent(s) comprises a methoxy-PEG-polyglutamate block polymer (PLGA-PEG) comprising 113 PEG units (mol wt about 5000 Da) and 100 glutamate units (mol wt about 15000 Da). In another particular embodiment, the polymeric charge-neutralising agent(s) comprises a polyglutamate-PEG-polyglutamate triblock polymer comprising 20 glutamate units (mol wt about 3000 Da), 113 PEG units (mol wt about 5000 Da) and then a further 20 glutamate units (mol wt about 3000 Da). Such block co-polymers can be produced by, for example, reversible addition-fragmentation chain-transfer (RAFT) polymerisation which enables control over the molecular weight of the polmeric products.

In some embodiments, the polymeric charge-neutralising agent(s) may exclude DSPE-PEG copolymers or, more specifically, may exclude DSPE-PEG$_{2000}$. That is, the polymer charge-neutralising agent may be a PEG derivative other than a DSPE-PEG copolymer or DSPE-PEG$_{2000}$.

The polymer charge-neutralising agent(s) may be readily incorporated into the non-viral nucleic acid delivery agent of the present disclosure by, for example, steadily adding the polymer charge-neutralising agent(s) during the complexation between the nucleic acid cargo and the lipopeptide compound(s). Indeed, surprisingly, it has been found that the novel combination of a nucleic acid cargo, a lipopeptide compound(s) such as a cationic lipopeptide, and a biocompatible and/or biodegradable polymeric charge-neutralising agent(s) such as a poly(glutamate)-PEG copolymer may enable the formation of the complexed particles at high concentration in a single production step. Using poly(glutamate)-PEG, it was also found that finer particles of nanoparticle dimensions (ie particles with an average particle diameter of 50-100 nm) could be produced.

As mentioned above, the particles of the non-viral nucleic acid delivery agent are characterised by a substantially neutral or negative particle surface charge. Those skilled in the art will understand that particles with a substantially neutral surface charge may be regarded as showing a zeta potential (ZP) in the range of −5 to 5 mV as measured by standard zeta potential measurement techniques well known to those skilled in the art (but preferably by using an electrophoretic technique combined with dynamic light scattering (DLS) as described in Example 1 hereinafter). Particles characterised by a negative surface charge may show a zeta potential (ZP) in the range of −40 to −5 mV.

By having a substantially neutral or negative surface charge, the particles of the non-viral nucleic acid delivery agent according to the disclosure, are less likely to electronically associate with extracellular proteins such as negatively charged serum proteins, and may show improved biodistribution and efficiency relative to prior LNP-based agents. Preferably, neutral particles will show a zero potential surface charge in the range of −2 to 2 mV, more preferably in the range of 0 to 1 mV. When negative particles are preferred, these will show a zeta potential surface charge in the range of −40 to −10 mV.

The non-viral nucleic acid delivery agent may preferably comprise the lipopeptide compound(s) and the nucleic acid cargo in a molar charge ratio within the range of 1:1 (lipopeptide:nucleic acid) to 4:1, and more preferably within the range of about 1.5:1 to about 3.5:1. In some particular embodiments, the lipopeptide compound(s) and the nucleic acid cargo may be present in a molar charge ratio of about 2:1 (lipopeptide:nucleic acid).

The non-viral nucleic acid delivery agent may preferably comprise the polymeric charge-neutralising agent(s) and the lipopeptide compound(s) in a molar charge ratio within the range of 1:4 (polymer:lipopeptide) to 1:1, and more preferably within the range of about 1:3 to about 1:2. In some particular embodiments, the polymeric charge-neutralising agent(s) and the lipopeptide compound(s) may be present in a molar charge ratio of about 0.75:2 or about 1:2 (polymer:lipopeptide).

In some embodiments, the polymeric charge-neutralising agent(s), lipopeptide compound(s) and nucleic acid cargo may be present in the non-viral nucleic acid delivery agent in a molar charge ratio of about 0.75:2:1 or about 1:2:1 (polymer:lipopeptide:nucleic acid).

The non-viral nucleic acid delivery agent may optionally incorporate receptor-mediated nucleic acid transfer ligands, antibodies or engineered fragments of antibodies for targeted delivery. The use of receptor-mediated nucleic acid transfer ligands aims to achieve cell or cell-specific delivery of the nucleic acid cargo by using ligands targeted to cell surface receptors. The ligands may be conjugated to the nucleic acid molecule, lipopeptide compound(s) and/or polymeric charge-neutralising agent(s). Examples of ligands for receptor mediated gene transfer include transferrin, neurotensin and mannan targeting, respectively, transferrin, neurotensin and the mannose receptors. Transferrin receptors are found on most cells; neurotensin receptors are found on neurons such as glutamatergic neurons in the brain; and mannose receptors are found on cells such as macrophages, dendritic cells and some endothelial cells.

In one particular embodiment, the non-viral nucleic acid delivery agent of the present disclosure may be regarded as a DNA or RNA vaccine for the delivery to a cell of a DNA or RNA molecule of vaccine significance (eg a DNA or mRNA molecule comprising a nucleotide sequence encoding an antigen or epitope).

In another particular embodiment, the non-viral nucleic acid delivery agent of the present disclosure is an agent for the delivery of a self-amplifying replicon RNA to a cell.

In yet another particular embodiment, the non-viral nucleic acid delivery agent of the present disclosure is an agent for the delivery of a modRNA to a cell.

In a second aspect, the present disclosure provides a method of delivering a nucleic acid molecule to a cell of a subject, said method comprising the steps of:

providing a non-viral nucleic acid delivery agent according to the first aspect; and delivering the non-viral nucleic acid delivery agent to said cell of the subject.

The non-viral nucleic acid delivery agent may be delivered to the cell using a simple needle injection (eg for parenteral administration such as intramuscular (im) administration), gene gun, electroporation, ultrasound or hydrodynamic delivery methodology.

The non-viral delivery nucleic acid agent may be delivered in combination with one or more suitable carriers or excipients.

Thus, in a third aspect, the present disclosure provides a pharmaceutical composition comprising a non-viral delivery nucleic acid agent according to the first aspect in combination with a pharmaceutically acceptable carrier or excipient.

The cell to which the non-viral nucleic acid delivery agent is delivered may be a rapidly dividing cell type such as a cancer cell. However, the cell may otherwise be of a type that is not regarded as being rapidly dividing (including, for example, cell types of the muscle, cell types of the kidney and liver, cell types of the immune system and cell types of the lung).

In a fourth aspect, the present disclosure provides a method of producing a non-viral delivery nucleic acid agent according to the first aspect, said method comprising:

combining a nucleic acid cargo, one or more lipopeptide compound(s), and one or more polymeric charge-neutralising agent under conditions suitable for the formation of complexed particles.

The lipopeptide compound(s) and the nucleic acid cargo may be combined in a molar charge ratio within the range of 1:1 (lipopeptide:nucleic acid) to 4:1, and more preferably within the range of about 1.5:1 to about 3.5:1. In some particular embodiments, the lipopeptide compound(s) and the nucleic acid cargo may be combined in a molar charge ratio of about 2:1 (lipopeptide:nucleic acid).

The polymeric charge-neutralising agent(s) and the lipopeptide compound(s) may be combined in a molar charge ratio within the range of 1:4 (polymer:lipopeptide) to 1:1, and more preferably within the range of about 1:3 to about 1:2. In some particular embodiments, the polymeric charge-neutralising agent(s) and the lipopeptide compound(s) may be combined in a molar charge ratio of about 0.75:2 or about 1:2 (polymer:lipopeptide).

In some embodiments, the polymeric charge-neutralising agent(s), lipopeptide compound(s) and nucleic acid cargo may be combined in a molar charge ratio of about 0.75:2:1 or about 1:2:1 (polymer:lipopeptide:nucleic acid).

Preferably, the step of combining the nucleic acid cargo, one or more lipopeptide compound, and one or more polymeric charge-neutralising agent (and the subsequent formation of complexed particles) is conducted in the aqueous phase.

The non-viral nucleic acid delivery agent of the present disclosure is hereinafter further described with reference to the following non-limiting examples and accompanying figures.

EXAMPLES

Example 1

Two DNA complexes were developed and assessed in vivo: a cationic LP/DNA complex and a neutralised PEGylated LP/DNA complex. The PEGylated LP/DNA complex was developed via the addition of distearoyl-phosphoethanolamine-(polyethylene glycol) (DSPE-PEG$_{2000}$) to the LP/DNA complex during self-assembly.

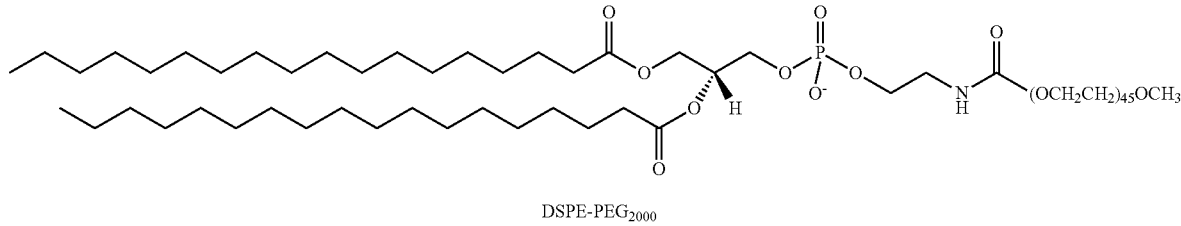

DSPE-PEG$_{2000}$

40

To assist in understanding the effect of shielding the cationic surface charge of complexes in DNA vaccine delivery, the relationships between the distribution, transfection and immunogenicity of the two DNA complexes were investigated and compared with injections of naked DNA in solution.

Methods and Materials

Materials

Stearoyl-CH$_2$K$_3$ LP was custom manufactured by G.L. Biochem (Shanghai, China), whilst the DSPE-PEG$_{2000}$ was obtained from Avanti Polar Lipids (Alabaster, Ala., United States of America). All materials were dissolved for use in 4-(2-hydroxyethyl)-1-piperazineethanesulfonic acid (HEPES)-glucose buffer (HGB) (15 mM HEPES and 5% w/v glucose, pH=7.4). The plasmid DNA used in the fluorescent distribution studies was pcDNA3.1HygrolacZ (Thermo Fisher Scientific, Carlsbad, Calif., United States of America) containing the beta-galactosidase expression cassette regulated by the cytomegalovirus promoter. For tissue-calibrated qPCR studies, pCMV-luc (constructed by ligating the firefly luciferase cDNA from pGL2 basic (Promega, Fitchburg, Wis., United States of America) into the multiple cloning site of pcDNA3 (Thermo Fisher Scientific) was used. In vivo gene expression studies used pNL1.1.CMV (Promega), a DNA plasmid of 3861 base pairs which contains the nanoluciferase gene under the control of the cytomegalovirus promoter (pCMV). The plasmid used for immunogenicity studies was pCMV-OVA which expresses a secreted form of ovalbumin [13]. Ovalbumin protein and OVA257-264 synthetic peptide (SIINFEKL; SEQ ID NO: 10) used in these studies were purchased from Sigma-Aldrich (St. Louis, Mo., United States of America). Lipopolysaccharide (LPS) used as an immunostimulatory adjuvant [14] co-injected with the ovalbumin positive control, was also purchased from Sigma-Aldrich. Carboxyfluorescein succinimidyl ester (CFSE) dye was obtained from Thermo Fisher Scientific.

Mice

The animals used were C57BL/6J male mice aged between 8-12 weeks. Injections were carried out intramuscularly into the left calf muscle, using a 50 µg dose of the naked plasmid DNA or DNA complexes in a 50 µL volume, unless otherwise stated. All mice were anaesthetised with 1-4% titrated isoflurane gas prior to intramuscular injection.

Calculation of Molar Charge Ratio

In the context of the LP/DNA complexes, the charge ratio refers to the number of positively charged amine groups ($NH_3^+$) provided by the cationic transfection agent per negatively charged phosphate group ($PO_4^-$) of DNA (where 1 phosphate group=1 nucleotide). For example, to obtain a theoretical charge ratio of 1:1 (LP:DNA) using stearoyl-$CH_2K_3$ (1045.45 g/mol, 3 $NH_3^+$/molecule), 1 µg of plasmid DNA (3 nmol) is mixed with 1.06 µg of stearoyl-$CH_2K_3$ (1 nmol). An average mass of 330 g/mol per nucleotide of DNA was used for the calculations. In the context of the DSPE-$PEG_{2000}$/LP/DNA complexes, the charge ratio refers to the number of negatively charged phosphate group provided by the DSPE-$PEG_{2000}$ per positively charged amine of the LP per phosphate group of the DNA, respectively. For example, to obtain a theoretical charge ratio of 1:1:1 (DSPE-$PEG_{2000}$:LP:DNA) with DSPE-$PEG_{2000}$ (2805.54 g/mol, $PO_4^-$/molecule) and stearoyl-$CH_2K_3$, 1 µg of plasmid DNA (3 nmol) is mixed with 1.06 µg of stearoyl-$CH_2K_3$ (1 nmol) and 8.5 µg of DSPE-$PEG_{2000}$ (3 nmol).

Preparation of DNA Complexes

LP/DNA complexes were prepared by mixing together the LP and DNA over a range of (+/−) charge ratios from 0.5:1 to 5:1 (LP:DNA). DSPE-$PEG_{2000}$/LP/DNA complexes were prepared by mixing together DSPE-$PEG_{2000}$, LP and DNA over a range of charge ratios, from 0.5:2.5:1 to 5:2.5:1 (DSPE-$PEG_{2000}$:LP:DNA). DNA complex mixtures were then incubated at room temperature for 30 minutes prior to use. To concentrate the DNA complexes for in vivo injections, ultrafiltration (5,000 g for ~5.5 hours at 4° C.) was carried out with an Amicon Ultra-15 centrifugal unit (Merck Millipore, Billerica, Mass., United States of America) with nominal molecular weight limit (NMWL) of 3 kDa.

Particle Characterisation

Dye Exclusion Assay

To determine the charge ratio at which the LP effectively condenses the DNA, a dye exclusion assay was carried out. In a 96-well black-bottomed plate, plasmid DNA (20 µg/mL) was prepared in 12 mM Tris-HCl (pH 7.4) buffer. To each well containing DNA, 0.05 µL of 10,000× concentrated stock of intercalating SYBR® Gold (Thermo Fisher Scientific) was added and the plate was incubated at room temperature for 15 minutes. The LP was then added to the wells at a series of charge ratios from 0.5:1 to 5:1. A well containing 20 µg/mL of naked DNA and SYBR® Gold was used as a 100% fluorescence intensity standard (ie no LP added). A blank well containing only the SYBR® Gold in buffer was used to subtract from the fluorescent readings of each sample. The plate was incubated at room temperature for 30 minutes for particle formation. The fluorescence (excitation 492 nm, emission 540 nm) of each sample was measured using a Wallac Envision 2102 Multilabel Reader (PerkinElmer, Waltham, Mass., United States of America).

Particle Sizing and Zeta Potential

The mean particle size (Z-average) and the zeta potential of each complex was measured via DLS using a Zetasizer Nano ZS (Malvern Instruments, Malvern, United Kingdom). For particle sizing, measurements were carried out at 25° C. with each measurement consisting of 10 runs, with a duration of 10 seconds each. The polydispersity index (PDI) of the size of the samples was recorded for each measurement. To ensure that the instrument was calibrated, a 60 nm±2.7 nm size standard (Malvern Instruments) was used prior to experimentation. For zeta potential measurements, to ensure the instrument was calibrated, a −68 mV±6.8 mV zeta potential standard (Malvern Instruments) was analysed prior to experimentation. All measurements were carried out at 25° C.

Cryo-TEM

Cryogenic transmission electron microscopy (Cryo-TEM) was carried out to image the DNA complexes. The complexes were prepared as stated above and 5 µL of each sample was deposited onto a holey carbon coated copper 300 mesh grid. The grid was then rapidly frozen in a liquid ethane bath cooled with liquid nitrogen. The temperature of each sample was maintained in a cryo-holder until time of imaging.

Salt Stability Assay

To test the stability of DNA complexes against salt-induced aggregation, particle sizing was carried out on the particles before and after the additional of NaCl. Briefly, DNA complexes were prepared in HGB, and DLS was used to measure particle size. NaCl solution was then added to the particles to a final concentration of 0.15 M. The particles were incubated for 30 minutes before DLS measurements were carried out again.

Transgene Expression

The luciferase assay was carried out to assay for the reporter nanoluciferase protein. At time points 1, 30 and 90 days post-injection, the calf muscle of each mouse was dissected and rapidly frozen in liquid nitrogen. The muscle was then homogenised in buffer (50 mM potassium phosphate, 1 mM DTT, 1 mM ethylenediaminetetraacetic acid, 10% glycerol) using a rotor/stator type tissue homogenizer (TissueTearor, Biospec Products, Bartlesville, Okla., United States of America). Quantification of the nanoluciferase reporter protein was carried out using the commercial Nano-Glo® Luciferase assay system with the Glo Lysis Buffer (both from Promega), in accordance with the manufacturer's instructions. Luminescence was measured using aLUMIStar Omega instrument (BMG Labtech, Ortenberg, Germany). To allow for the comparison between samples, a Bradford assay was employed to determine the total protein in the tissue lysates for the standardisation of expression levels. The assay was carried out using the Quick Start™ Bradford assay (Bio-Rad, Hercules, Calif., United States of America) according to manufacturer's instructions, using bovine serum albumin as the protein standard. The resultant absorbance was measured using an EnVision® Multilabel Reader (PerkinElmer) at a wavelength of 595 nm.

Tissue-Calibrated qPCR

Tissue-calibrated qPCR was carried out according to the procedure outlined by Ho et al. [15]. Briefly, mice received an intramuscular injection of naked plasmid DNA or DNA complexes using pCMV-luc. Thirty minutes after injection, tissues were harvested and homogenised in DNAzol reagent (Thermo Fisher Scientific) using a handheld TissueTearor homogenizer (Biospec Products) or with a Pellet Pestles motor grinder (Sigma-Aldrich), and incubated overnight with proteinase K (Qiagen, Venlo, Netherlands) (100 µg/ml) at room temperature. Tissue extracts were then centrifuged for 10 minutes at 10,000 g at 4° C., and total DNA was extracted from the supernatant using a Wizard DNA Prep Spin column (Promega), following the manufacturer's instructions. Real-time quantitative PCR was carried out with a CFX96™ Real Time PCR Detection System (Bio-Rad). Forward (5' CCTCATAAAGGCCA AGAAGG 3'; SEQ ID NO: 11) and reverse (5' ACACCGGCCTTATTC-CAAG 3; SEQ ID NO: 12) primers were used to amplify a 114 bp fragment of the pCMVluc. Each PCR reaction consisted of 5 µL of the iQ SYBR Green Supermix (Bio-Rad, Hercules, Calif.), 200 nmol/l of each primer, 1 ng of template DNA and water to a total reaction volume of 10 µL. Reactions were carried out with an initial incubation at 95° C. for 3 minutes, followed by 40 cycles of denaturation at 95° C. for 10 seconds, annealing at 47° C. for 30 seconds, and extension at 72° C. for 30 seconds. All reactions were carried out in triplicate and "no template" controls, containing water instead of template DNA, were included in every PCR run. Absolute quantitation of the plasmid present in the tissue was carried out using standard curves constructed for each tissue assayed. Standard curves were prepared by the addition of serially diluted plasmid standards to homogenates of each pre-weighed, excised tissue of interest.

Tracking Localisation of DNA Complexes in Tissue

To track the DNA complexes after administration, pcDNA3.1HygrolacZ was covalently labelled with fluorescent nucleotide ChromaTide® Alexa Flour® 594-5-dUTP (Thermo Fisher Scientific). Briefly, plasmid DNA was digested with the BglII restriction enzyme (New England Biolabs, Ipswich, Mass., United States of America) (2 units per 1 µg of DNA) and incubated overnight at 37° C. to yield a linear plasmid with 5' GATC overhangs. The plasmid was purified via phenol-chloroform extraction, followed by ethanol precipitation. The Klenow fragment (New England Biolabs) was then added to the linearised plasmid, in addition to 60 nM of each dNTP—substituting dUTP with the fluorescent Alexa Flour® 594-5-dUTP—and the mixture was incubated at room temperature for 4 hours. The reaction was terminated by adding ethylenediaminetetraacetic acid to a final concentration of 10 mM. Phenol-chloroform extraction and ethanol precipitation was carried out to purify the resultant labelled plasmid (DNA-AF594). To minimise the presence of any free unincorporated nucleotides in the solution, the DNA pellet was washed three times with 70% ethanol prior to DNA resuspension. Mice received an intramuscular injection of naked DNA-AF594 or DNA-AF594 complexes at a dose of 50 µg in 50 µL. The mice were then euthanised 30 minutes after injection. The muscle was dissected, fixed in 4% PFA and frozen with dry ice in Tissue-Tek® OCT™ Compound (Sakura Finetek USA Inc, Torrance, Calif., United States of America). Cryosectioning was carried out at −20° C. 10 µm sections were collected for every 800 µm of tissue. Tissue sections were mounted in Vectashield (Vector Laboratories, Burlingame, Calif., United States of America) and imaged using a Nikon A1R confocal microscope (Nikon, Minato, Japan). Total pixel count of the DNA-AF549 was carried out for each image using the Image J software (NIH), with a set threshold level of 60, as determined by imaging the vehicle-treated muscle. Additionally, the extent of localisation of the fluorescent DNA in each of the images was classified as associated with either epimysium, perimysium or endomysium. The classifications were as follows: +++ indicated a high degree of association, ++ indicated a medium degree of association, + indicated a low degree of association and − indicated that no detectable levels of the labelled DNA were associated with this region). A value was then assigned to each category with +++ equal to 3, ++ equal to 2, + equal to 1 and − equal to 0. The sum of these numbers (i.e. weighted pixel count) for each extracellular region was determined for each muscle, and the mean was plotted graphically.

In Vivo Cytotoxic T Lymphocyte Elimination Assay

To evaluate the overall cellular response elicited in mice injected with the DNA complexes, an in vivo cytotoxic T lymphocyte (CTL) activity assay was carried out according to the procedure outlined in White et al. [16].

Mouse Injection and In Vivo Assay Schedule

On day one, mice were primed with the DNA complexes or control formulations. LP/DNA and DSPE-PEG$_{2000}$/LP/DNA complexes were prepared as previously described using the pCMV-OVA plasmid. The positive control formulation used in this experiment was an injection of 2×10$^7$ ovalbumin-coated splenocytes with 1 µg of LPS. The ovalbumin-coated splenocyte was prepared by incubating a single-cell suspension of isolated splenocytes (from naïve C57BL/6J mice) with ovalbumin. Splenocytes were suspended in red blood cell lysis buffer and incubated at 37° C. for 2 minutes, washed and passed through a 70 µm cell strainer to filter off any cell debris. Cells were then incubated with ovalbumin (10 mg/mL) at 37° C. for 10 minutes, washed, and then resuspended in PBS. On day 6 post-immunisation, mice were injected intravenously with target splenocytes (preparation outlined below). The following day, splenocytes were harvested from the mice and analysed via flow cytometry (preparation outlined below). The percentage of target ovalbumin-pulsed splenocytes eliminated was then calculated for each mouse.

Preparation of Target Splenocytes

Target splenocytes were prepared via depleting a single cell suspension of isolated splenocytes of red blood cells, and dividing the population of cells equally into two tubes. To one tube, OVA257-264 peptide was added to a concentration of 1 µg/mL. Both tubes were then incubated at 37° C. for 1 hour, washed, and resuspended in 10$^7$ cells per mL in PBS and 1% FBS. To the OVA$_{257-264}$ peptide-pulsed tube of splenocytes, 0.5 µL of 10 mM CFSE was added per 1 mL of cells (ie high CFSE concentration). To the unpulsed population of splenocytes, 0.5 µL of 1 mM CFSE was added per 1 mL of cells (ie low CFSE concentration). The two tubes were then incubated at 37° C. for 10 minutes, washed and then resuspended in PBS. The two populations of cells were then mixed together at a 1:1 ratio (high CFSE:low CFSE populations), and each mouse received an intravenous injection of 2×10$^7$ mixed cells in 200 µL of PBS.

Flow Cytometry

Flow cytometry was carried out using the BD FACSCanto™ II (BD Biosciences, San Jose, Calif., United States of America) to identify the ratio of OVA-pulsed (high CFSE-labelled) population of splenocytes to unpulsed (low CFSE-labelled) splenocytes. For each sample, 2 million events were recorded. The percentage of cells eliminated from OVA-specific T cell activation in each mouse was then calculated using the following formula:

$$1 - \frac{\text{Ratio of pulsed:unpulsed splenocytes in negative control mouse}}{\text{Ratio of pulsed:unpulsed splenocytes in experimental mouse}} \times 100$$

Antibody Response Assay

Mice were given an initial administration (prime) of either naked plasmid (control), the LP/DNA or DSPE-PEG$_{2000}$/LP/DNA complex (test formulations), ovalbumin protein (positive control) or saline (negative control) on day one, using ovalbumin-expressing pCMV-OVA as the plasmid DNA. A booster injection was then administered four weeks later. The administration of naked DNA, the DNA complexes and saline were all carried out intramuscularly into the calf muscle of mice using a dose of 50 µg in 50 µL. The administration of the ovalbumin positive control (50 µg ovalbumin protein+1 µg LPS) was carried out intramuscularly in a 50 µL injection volume. Blood (~100 µL) was collected from mice via sub-mandibular bleeding of the mice using a 5 mm lancet on: day one (prior to prime injection), at four weeks (prior to boost injection), then at nine, eleven and thirteen weeks after the initial prime. Blood samples were then incubated at 37° C. for 90 minutes and then stored at 4° C. for ~18 hours—following procedure outlined in White et al. (2008)[16]. Serum was then collected by centrifugation (10,000 g for 15 minutes at 4° C.) and stored at −20° C. until further use. For the quantitation of anti-ovalbumin immunoglobulins (IgG, IgM and IgA class antibodies) in serum, the mouse Anti-ovalbumin Ig ELISA kit (Alpha Diagnostic, San Antonio, Tex., United States of America) was used. The assay was carried out in accordance with the manufacturer's instructions. The absorbance at 450 nm was measured with the Envison Wallac Plate Reader (PerkinElmer). Data was expressed in relation to the values of the positive index (ie Mean+2 SD of absorbance values of control pre-immunised mice). The quantitation of the anti-OVA activity level was calculated by the following equation, with values 1.0 indicated positive antibody activity in mice, whilst values below 1.0 were negative for antibody activity.

$$\frac{\text{Sample absorbance}}{\text{Positive index}}$$

Statistical Analysis

For the in vitro characterisation of complexes, the data in graphs are represented as mean±standard error of the mean (SEM) with each data point representing n=3 samples, unless otherwise stated. For all in vivo experiments, the data in graphs are represented as mean±SEM with each data point representing n=6-8 samples, unless otherwise stated. A paired student t-test was used to determine the significant differences in the Z-average or PDI of the DNA complexes after addition of NaCl. Two-way ANOVA with Dunnett's post hoc test was used to assess the statistical significance of the transgene expression levels of the DNA complexes in the nanoluciferase assay over time. Two-way ANOVA with Tukey's post hoc test was used to assess the statistical significance of the differences in the weighted total pixel count of the fluorescent plasmid between the formulations and their extent of localisation in the extracellular regions of the muscle. The Kruskal-Wallis test, along with Dunn's post hoc test, was used to compare the significant differences in the number of anti-OVA positive mice between each group. One-way ANOVA with Dunnett's post hoc test was used to evaluate statistical significance in epitope-specific T lymphocyte activity in mice in comparison to saline. One-way ANOVA with Tukey's post hoc test was used to evaluate the statistical significance of epitope-specific T lymphocyte activity in mice between groups, and the differences in fluorescence intensities in the dye exclusion assay. For all tests, p-values of less than 0.05 were considered to be statistically significant.

Results

Formation and Characterisation of Self-Assembled LP/DNA Complexes

Dye exclusion assay of the LP/DNA complexes revealed a steep decline in fluorescence with the increasing addition of the LP to DNA between (+/−) charge ratios of 1:1 to 2.5:1. Fluorescence reached a minimum at ratios greater than 2.5:1, indicating that no further condensation of the DNA occurred beyond this stage (FIG. 1A). Substitution of the cysteine in stearoyl-CH$_2$K$_3$ with serine, a residue of similar polarity, resulted in a higher observed fluorescence intensity from a charge ratio of 2:1 onwards (n=3, p<0.05) (data not shown). Similarly, substitution with the more non-polar alanine too resulted in higher fluorescence at these later charge ratios (n=3, p<0.05). The steep decline in fluorescence across low charge ratios, observed with the stearoyl-CH$_2$K$_3$, was not observed with these two substituted LPs. Instead, a more gradual decrease in fluorescence was observed. This indicated that the cysteine residue plays a role in assisting the condensation of plasmid DNA. Addition of the reducing agent dithiothreitol (DTT) to the stearoyl-CH$_2$K$_3$ LP before DNA complexation significantly increased the degree of fluorescence observed for the LP/DNA particles at a charge ratio of 2.5:1 (n=3, p<0.05) (data not shown). This indicates that it is the formation of a disulphide bond between a pair of LPs that assisted the condensation of the DNA in the LP/DNA complexes.

DLS and zeta potential measurements revealed that a generally polydisperse (PDI>0.25) population of large, negatively charged and/or neutral population of particulates formed with apparent diameters of >1 µm when charge was close to neutral (FIG. 1B, C). Cryo-TEM imaging of the complexes formed at a charge ratio of 1.5:1 showed the formation of non-spherical, irregularly shaped particles in the solution, comprising predominantly large aggregates of smaller particles (FIG. 1D, E). Interestingly, the aggregates appeared to comprise particles of approximately 30 nm in diameter. At higher charge ratios (>2:1), a narrower dispersion of small, positively charged DNA complexes formed, with zeta potentials of ≥+30 mV and particle diameters of approximately 100 nm (PDI≤0.25). Cryo-TEM imaging of the LP/DNA complexes formed at a charge ratio of 2.5:1, revealed a more uniform population containing a large proportion of smaller particles approximately 30 nm in diameter, with occasional clusters which were approximately 60-90 nm in size. These aggregates also appeared to be comprised of a few primary ~30 nm particles. Due to their relatively small size and high cationic surface charge, the LP/DNA complexes formed at a charge ratio (+/−) of 2.5:1 were selected for evaluation in vivo. These complexes had a diameter of 112.5±13.9 nm and a zeta potential of +34.2±1.2 mV.

Formation and Characterisation of PEGylated LP/DNA Complexes

Figure 2:
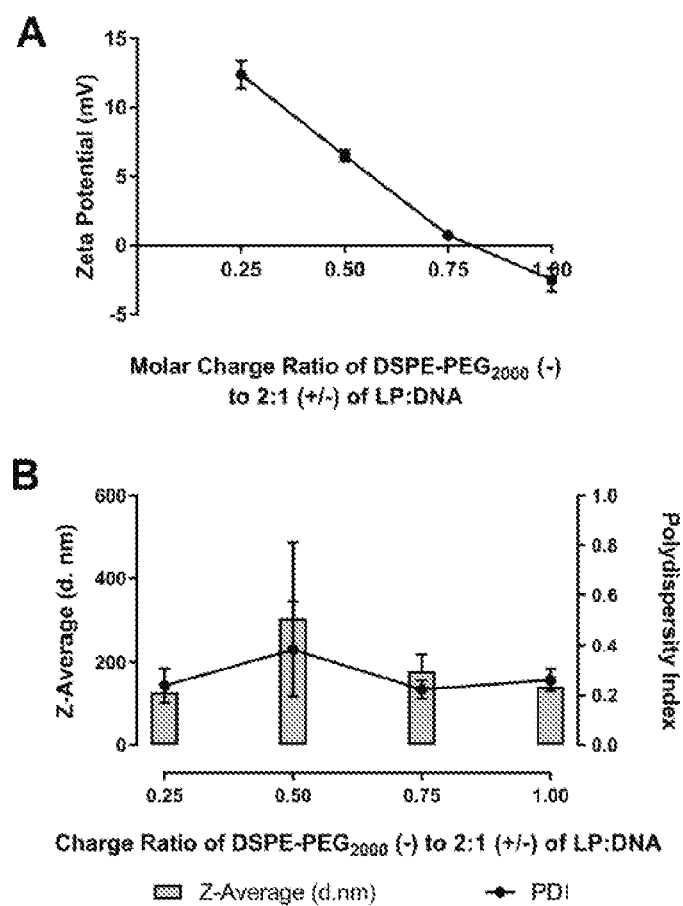
FIG. 2 provides results of characterisation studies of DSPE-$PEG_{2000}$/LP/DNA complexes according to the present disclosure. The PEGylated LP/DNA complexes were prepared at various charge ratios and the resultant A) zeta potential and B) particle size and polydispersity index are shown. A reduction in zeta potential was observed with the addition of negatively charged DSPE-$PEG_{2000}$ to the LP/DNA complex. Data is presented as mean±SEM, n=3.

Incremental addition of negatively charged DSPE-PEG$_{2000}$ to the LP/DNA particles lowered their positive zeta potential, such that the resulting particles reached a zeta potential close to ~0 mV at ratios 0.75:2:1 and 1:2:1 (FIG. 2A). DSPE-PEG$_{2000}$/LP/DNA complexes formed at a charge ratio of 0.75:2:1 were selected to test their stability against salt-induced aggregation, and were subsequently used in in vivo studies. These complexes had a diameter of 198.6±49.5 nm and a zeta potential of +0.76±0.2 mV (FIG. 2B). The addition of the PEGylated coating to the LP/DNA complexes resulted in particles with slightly larger hydrodynamic diameter, though their diameter was not statistically different to the cationic LP/DNA particles according to the Student's t-test.

PEGylation Confers Stabilisation Against Salt-Induced Aggregation

Figure 3:
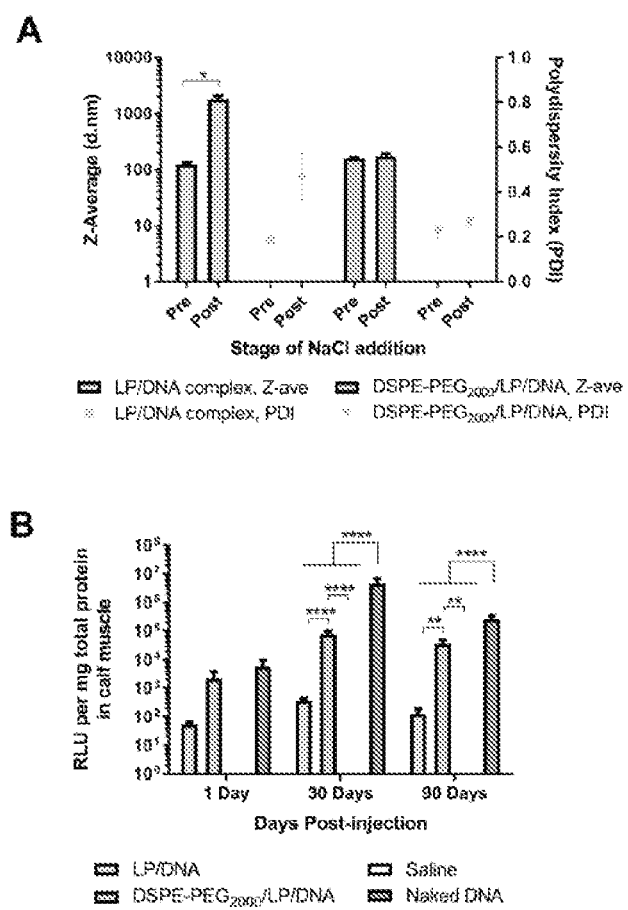
FIG. 3 provides graphical results showing particle stability on addition of NaCl and relative gene expression in muscle after intramuscular injection. A) The mean particle size and polydispersity index of LP/DNA prepared at a charge ratio of 2.5:1 and DSPE-$PEG_{2000}$/LP/DNA prepared at a charge ratio of 0.75:2:1 with and without the addition of 0.15M NaCl. *$p<0.05$ for the increase in Z-average in comparison untreated control (Paired student's t-test). Data is presented as mean±SEM. n=3. B) Relative gene expression determined as relative light units (RLU) in the calf muscle at 1, 30 and 90 days after injection of DNA complexes or naked DNA. Data is presented as mean±SEM of n=3-6 mice. $p<0.01$ and **$p<0.0001$ for significant expression levels between treatments as indicated (Two-way ANOVA, Tukey's post hoc test). Background RLU determined in saline treated controls was less than 1.

Incubation of the LP/DNA complexes in an isotonic buffer induced aggregation of the complexes. DLS analysis indicated that the apparent particle diameter increased significantly by 15-fold ($p<0.01$) (FIG. 3A). PEGylation of the LP/DNA complexes conferred salt stability to the DNA complexes. Particle size by DLS was not significantly different after addition of NaCl.

PEGylation Increases Transgene Expression of LP/DNA Complexes In Vivo

Assay of nanoluciferase expression revealed that administration of naked DNA, LP/DNA and PEGylated LP/DNA complexes resulted in significant gene expression in the calf muscle at all assayed time points over the course of the 3-month study (FIG. 3B). The PEGylated LP/DNA complexes exhibited higher gene expression levels in the muscle than the LP/DNA complexes at all time points, with maximal expression observed 1 month after injection ($n=3$ to 6, $p<0.0001$). At this time point, gene expression resulting from injection of the PEGylated complexes was over 200-fold higher than that of its non-PEGylated counterpart. However, naked DNA injections exhibited the highest extent of gene expression in the calf muscle overall. At 30 days, naked DNA produced 1,200- and 60-fold increase in nanoluciferase expression when compared to the LP/DNA ($n=3$ to 6, $p<0.0001$) and PEGylated LP/DNA complexes ($n=3$ to 6, $p<0.0001$), respectively. Gene expression was still evident at 90 days. The expression level from naked DNA was still highest but appeared to decline between day 30 and 90, whereas the levels induced by the particulate formulations maintained gene expression between 30 and 90 days.

Distribution of DNA Complexes in Tissue

Figure 4:
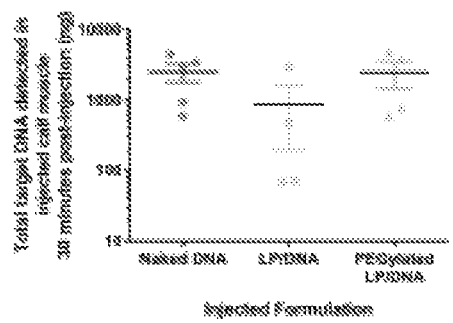
FIG. 4 provides graphical results showing local distribution of DNA complexes in vivo. A) Total target plasmid detected by qPCR in the injected calf muscle at 30 minutes after injection of naked DNA, LP/DNA or DSPE-$PEG_{2000}$/LP/DNA. Data is presented as mean±SEM of n=4-5 mice. B) Semi-quantitative analysis of the extent of localisation of DNA-AF594 in the muscle post-injection of each formulation to the respective regions: endomysium (En), perimysium (Pe) and epimysium (Ep). Data is presented as mean±SEM of n=3 mice, with a total of 12 muscle sections collected from each mouse. *$p<0.05$ and ***$p<0.001$ for significant differences in pixel count (One-way or Two-way ANOVA, with Tukey's post hoc test)
Figure 4:
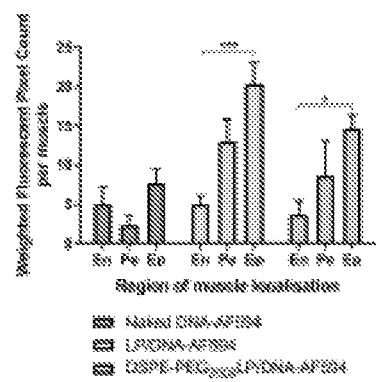

A qPCR assay for plasmid DNA concentration in the muscle, 30 minutes after injection of DNA complexes or naked DNA, revealed that a similar concentration of the plasmid were present, with no significant differences observed between the injected formulations (FIG. 4A). The mass of plasmid detected in the entire muscle after injection of each of the three formulations ranged between ~1 and ~5% of the dose administered. While not wishing to be bound by theory, it is considered that the higher transfection efficiency of the PEGylated complexes, when compared to their non-PEGylated counterparts, may have been due to widespread distribution of the PEGylated complexes throughout the muscle tissue, whereas distribution of the cationic complexes may have had restricted by charge-charge interactions between particles and extracellular matrix. To test this, imaging studies were carried out with the intention of tracking the dispersion of fluorescently labelled plasmid with the complexes 30 minutes after injection. Tissue slices were assessed qualitatively and a quantitative assessment was also carried out using a pixel counting technique. Inspection of the tissue slices indicated that administration of both complexes resulted in the localisation of the labelled DNA in mostly the epimysium regions of the muscle rather than the endomysium. Using a weighted pixel counting method this was verified for LP/DNA and DSPE-PEG$_{2000}$/LP/DNA complexes (FIG. 4B; $n=3$, $p<0.001$, $p<0.05$, respectively). In contrast, the injection of naked DNA into the muscle did not result in the preferential localisation of plasmid to any of the three regions in the muscle.

Humoral Immune Responses to Injection of pCMV-OVA

Figure 5:
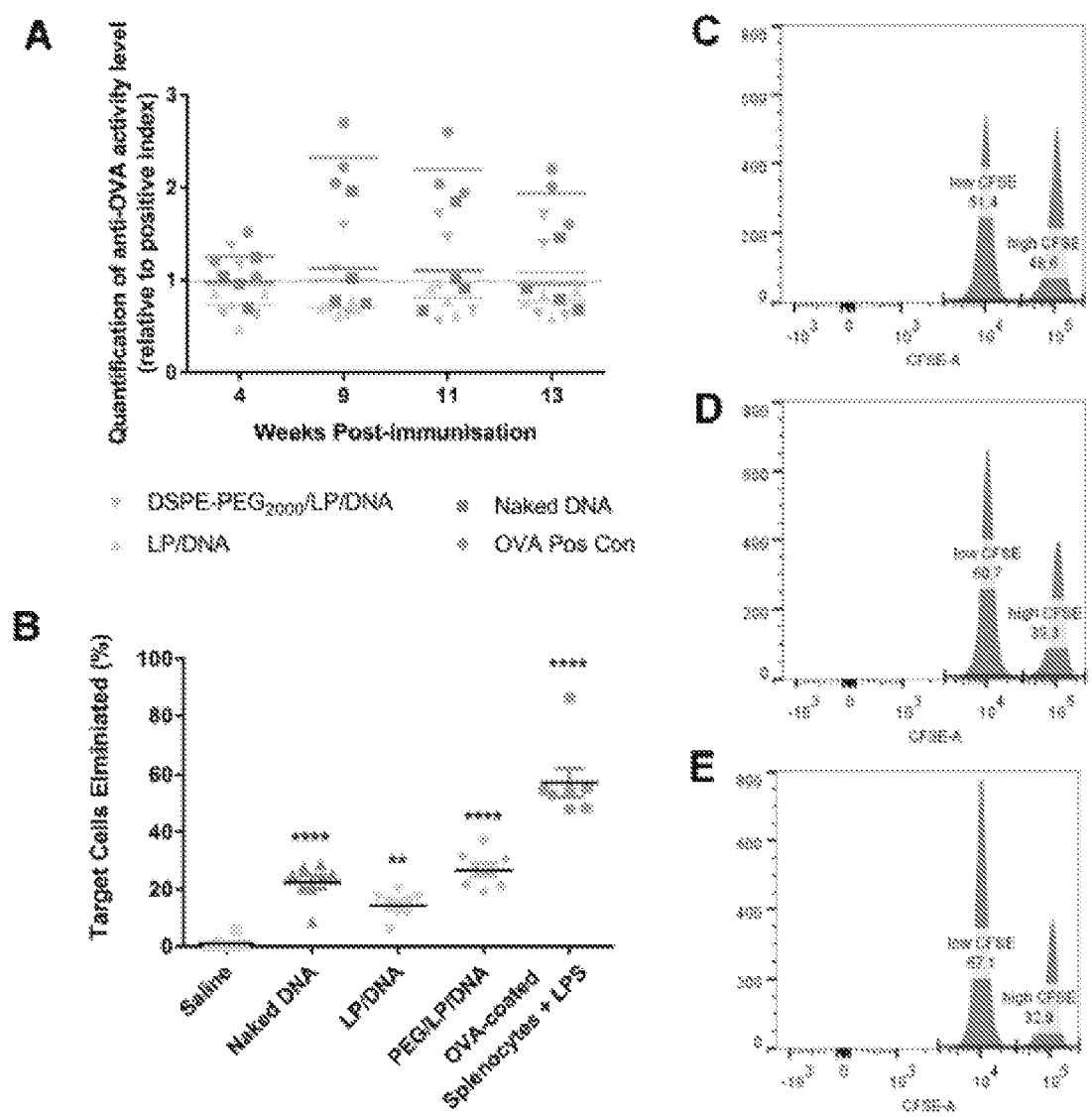
FIG. 5 shows the results of experiments investigating the immunogenicity of DNA complexes. A) Ovalbumin-specific antibody activity levels in serum of mice (relative to the positive index) after administration of DNA complexes or control formulations. Symbols represent the individual data points, whilst the line represents the mean. The dotted line denotes the positive index of 1. Values>1 are positive for anti-OVA activity; values<1 are negative for anti-OVA activity. B) Percentage of target epitope-specific cells eliminated in mice immunised with either: OVA-coated splenocytes (positive control), saline (negative control), LP/DNA, DSPE-$PEG_{2000}$/LP/DNA or naked DNA. Data is presented as the mean±SEM. $p<0.01$ and **$p<0.0001$ for significant activity levels compared to saline-treated mice (One-way ANOVA, with Dunnett's post hoc test). Representative histograms showing the distinct $OVA_{257-264}$ pulsed (high CFSE conc.) and unpulsed (low CFSE conc.) population of splenocytes detected in mice immunised with saline (C), LP/DNA (D) or DSPE-$PEG_{2000}$/LP/DNA (E) formulations.

Immunisation with 50 μg DNA in the form of the LP/DNA complexes using the selected prime-boost regimen did not elicit significant ovalbumin-specific immunoglobulin levels in mice. All mice exhibited activity below the positive index (FIG. 5A). Though not statistically significant according to the Kruskal-Wallis test, the injection of naked DNA and the DSPE-PEG$_{2000}$/LP/DNA complexes both resulted in positive mice (2 out of 4 mice), and overall the response to DSPE-PEG$_{2000}$/LP/DNA complexes appeared to be more successful than naked DNA, with two strong responders out of four at weeks 11 and 13. The positive control of the ovalbumin-coated splenocytes co-administered with LPS induced a robust response in all mice (3 out of 3 mice).

Cell-Mediated Immune Responses to Injection of pCMV-OVA

Flow cytometry showed that the injection of the pCMV-OVA plasmid in its naked or complexed form induced highly significant epitope-specific T cell elimination of the target ovalbumin-pulsed population of splenocytes, by comparison to the saline control (FIG. 5B to E). The results indicated that immunisation with both the DSPE-PEG$_{2000}$/LP/DNA and the naked DNA complexes induced a similar percentage of ovalbumin-specific elimination of cells in mice ($26.7\pm2.2\%$ ($n=8$, $p<0.0001$) and $22.5\pm2.3\%$ ($n=8$, $p<0.0001$)) of target cells eliminated, respectively. Immunisation with the LP/DNA complex induced a lower response with $14.3\pm1.6\%$ of cells eliminated. Although this response was significantly higher than the saline control ($n=8$, $p<0.01$), it was significantly lower than that of the DSPE-PEG$_{2000}$/LP/DNA ($n=8$, $p<0.05$). As expected, the positive control injection of OVA-coated splenocytes and LPS induced the most robust response, with $57.2\pm5\%$ of cells eliminated ($n=8$, $p<0.0001$).

Discussion

The results of this example show that the use of LPs and polymeric charge-neutralising agents such as DSPE-PEG$_{2000}$ as the basis of the development of novel nucleic acid delivery agents offers considerable promise. The inclusion of the DSPE-PEG$_{2000}$ in appropriate proportions advantageously enabled the production of small particles (ie particle diameters of ~200 nm) without extensive aggregation and which showed effective neutralisation of the strong cationic surface charge of the LP/DNA complexes. The PEG layer was also observed to confer stability against salt-induced aggregation indicating that the PEGylated LP/DNA complexes would be less likely to aggregate upon contact with biological fluid after administration in vivo. Moreover, the PEGylated LP/DNA complexes were able to induce higher transgene expression levels in the muscle than the LP/DNA complexes tested and in an in vivo CTL assay, elicited a higher cellular response than the LP/DNA complexes.

Example 2

Alternative DNA complexes were developed using LPs and poly(glutamate)-PEG (particularly, methoxy-PEG-poly(L-glutamate) block polymers, as supplied by Almanda Polymers; referred to as PLGA-PEG) instead of distearoyl-phosphoethanolamine-(polyethylene glycol) (DSPE-PEG$_{2000}$).

Materials and Methods

Figure 6:
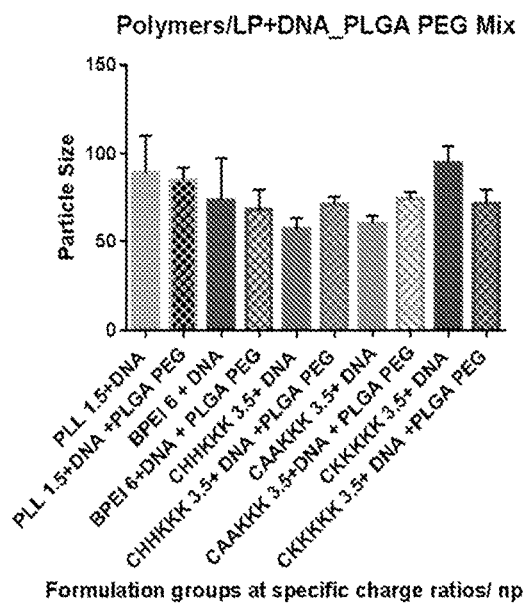
FIG. 6 provides graphical results obtained with PLGA-PEG/LP/DNA complexes and comparative particles prepared using polylysine (PLL) and polyethyleneimine (PEI): (A) shows the particle size of various complexed particles; and (B) shows the zeta potential (ZP) of the formed particles.
Figure 6:
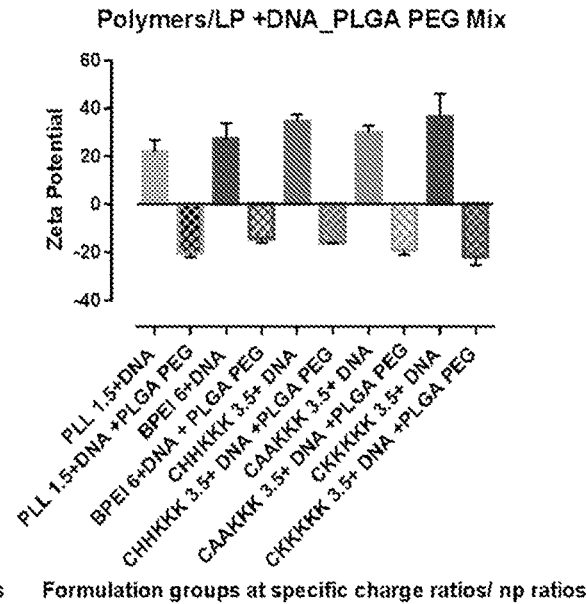
Figure 7:
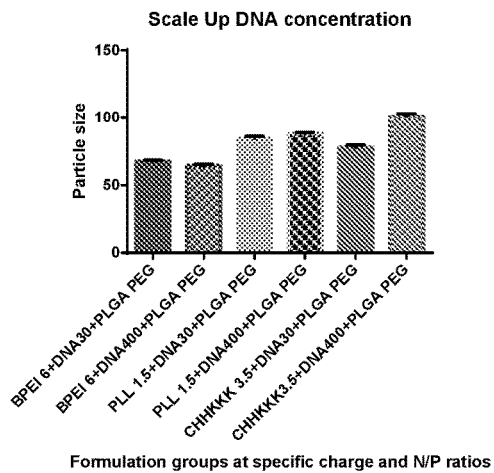
FIG. 7 provides graphical results obtained with PLGA-PEG/LP/DNA complexes and other comparative particles prepared with either 30 or 400 µg/ml of DNA: (A) shows the particle size of various complexed particles; and (B) shows the zeta potential (ZP) of the formed particles.
Figure 7:
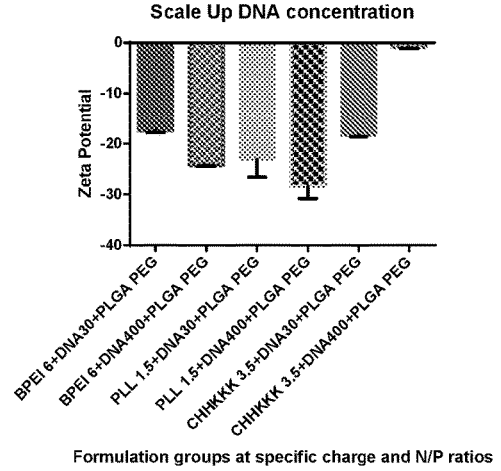

Particle complexes comprising a nucleic acid cargo (particularly, the plasmid DNA molecule pNL1.1.CMV (Promega) encoding the nanoluciferase gene), a cationic lipopeptide selected from stearoyl-Cys-His-His-Lys-Lys-Lys (designated CH2K3 in FIGS. 6 and 7; SEQ ID NO: 1), stearoyl-Cys-Ala-Ala-Lys-Lys-Lys (designated CA2K3; SEQ ID NO: 5) and stearoyl-Cys-Lys-Lys-Lys-Lys-Lys (designated CK5; SEQ ID NO: 13), and PLGA-PEG were produced substantially as described above in Example 1 (ie with PLGA-PEG substituted for DSPE-PEG$_{2000}$). Briefly, the DNA molecule and poly(L-glutamate-PEG) were dissolved together in HEPES buffer and added to an equal volume of the cationic lipopeptide dissolved in HEPES buffer to produce a final DNA concentration of 15 µg/ml. For comparison, preparations of the DNA molecule with polylysine (PLL) and polyethyleneimine (PEI) were also produced along with complexes of the DNA molecule with each of the above lipopeptides alone.

In further experimentation, the various particle complexes were produced using varying amounts of the DNA molecule (specifically, 30 or 400 µg/ml of the DNA molecule). The respective DNA solution was added to a solution (in equal volume) of either the cationic lipopeptide, stearoyl-Cys-Lys-Lys-Lys-Lys-Lys (SEQ ID NO: 13), or one of the polycationic ligands PLL or pEI, and PLGA-PEG. This resulted in particles with a final DNA concentration of 15 µg/ml or 200 µg/ml.

The various complexes were assessed for particle size and zeta potential using the methods described above in Example 1.

Results

All of the complexed particles were of a size in the range of 60 to 100 nm (average particle diameter size) (FIGS. 6A and 7B). With the inclusion of PLGA-PEG, the average particle diameter size for all of the lipopeptides tested was similar (about 70 nm where the particles had a final DNA concentration of 15 µg/ml), but increased in size where higher concentrations of the DNA molecule were used during preparation. All of the particles comprising PLGA-PEG were negatively charged (FIGS. 6B and 7B) or close to neutral. The neutral to negative charge can be tailored according to needs.

Example 3

Materials and Methods

Figure 8:
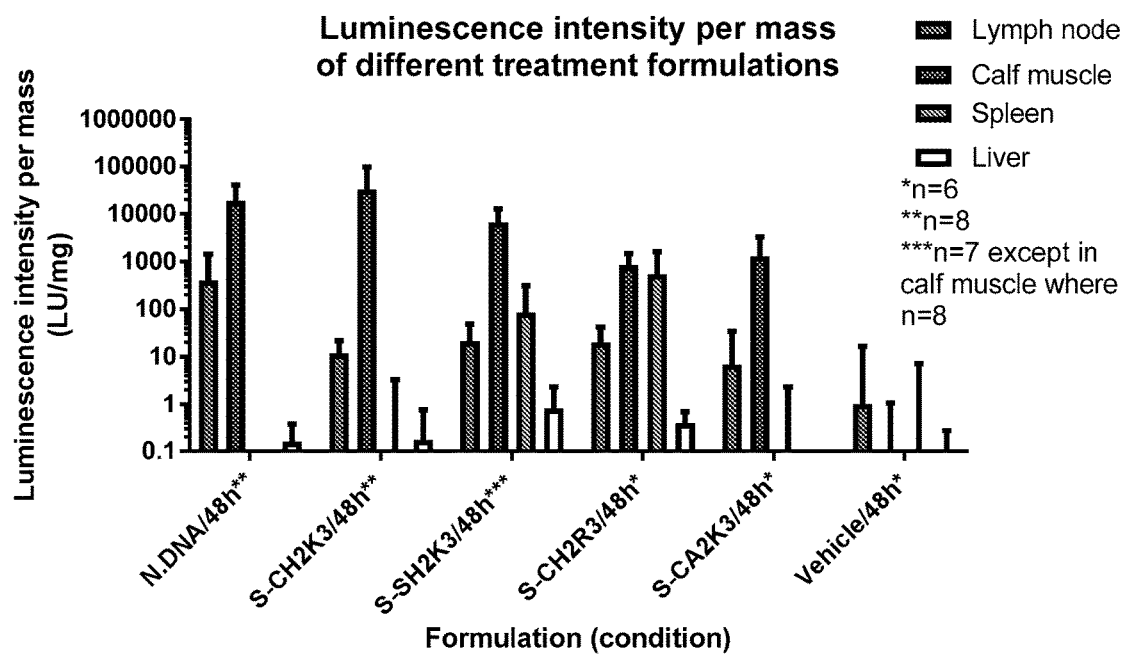
FIG. 8 provides graphical results obtained with PLGA-PEG/LP/DNA complexes (pNLL1.1.CMV encoding the nanoluciferase gene) following intramuscular injection into C57 mice. The graphs show the relative nanoluciferase activity per unit mass of tissue: A) after 48 h and B) after 7 days. (N.DNA=naked DNA in isotonic buffer solution)
Figure 8:
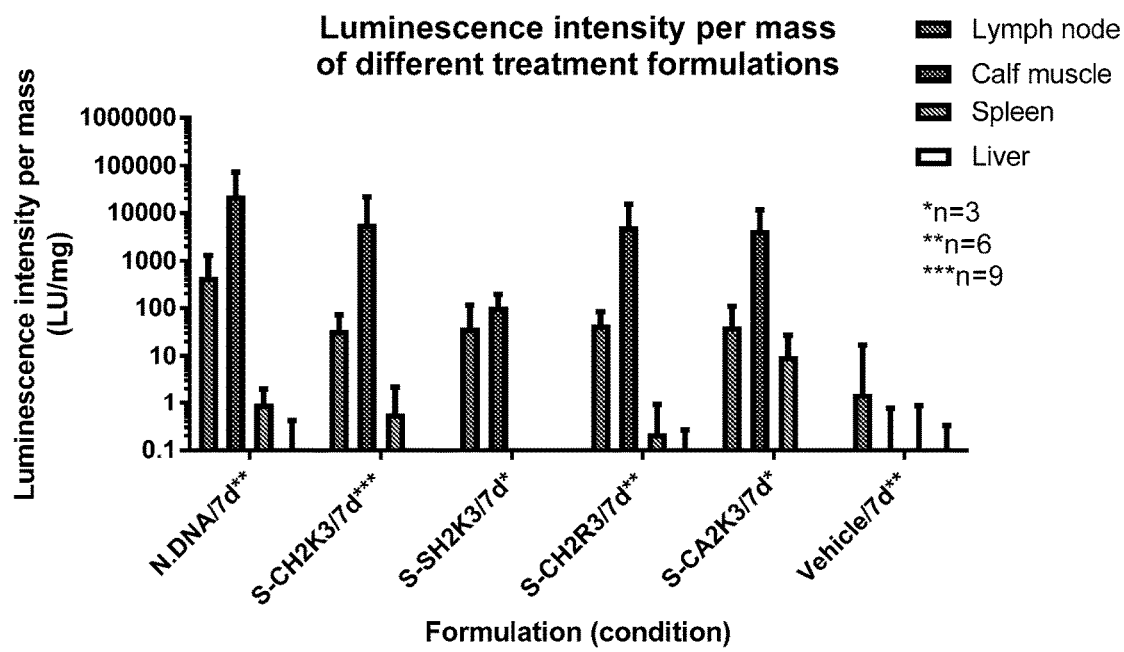

Further DNA complex particles comprising pNL1.1.CMV (Promega), a cationic lipopeptide selected from stearoyl-Cys-His-His-Lys-Lys-Lys (designated S—CH2K$_3$ in FIG. 8; SEQ ID NO: 1), stearoyl-Cys-Ala-Ala-Lys-Lys-Lys (designated S-CA2K$_3$ in FIG. 8; SEQ ID NO: 5), stearoyl-Ser-His-His-Lys-Lys-Lys (designated S—SH2K$_3$ in FIG. 8; SEQ ID NO: 7) and stearoyl-Cys-His-His-Arg-Arg-Arg (designated S—CH2R3 in FIG. 8; SEQ ID NO: 6), and PLGA-PEG (a block polymer with MW PLGA=15 kDa, MW PEG=5 kDa) were produced substantially as described above in Example 2. Briefly, the complexes were prepared in a form suitable for intramuscular (im) administration by mixing two aqueous solutions in 0.01M HEPES (pH 7.4); one containing the plasmid DNA and PLGA-PEG, and the other containing the appropriate lipopeptide (LP).

Each formulation was injected once intramuscularly into the gastrocnemius muscle of C57 mice, at a dose of 10 µg per injection. After either 48 h or 7 days, the animals were euthanised and the gastrocnemius muscle, draining lymph nodes, the spleen and liver were excised and homogenised (using gentleMACS C tubes; Miltenyi Biotec, Bergisg Gladbach, Germany). Thereafter, the supernatant was assayed for nanoluciferase expression using the Nano-Glo Luciferase assay system (Promega).

Results

The results are shown in FIGS. 8A and B; expressed as relative luminescence intensity per mg of tissue. The complex particles (generally <100 nm with zeta potentials between −5 mv and −20 mv) resulted in high levels of gene expression in muscle that was evident after 48 hours and 7 days; with all of the complex variations showing activity. The stearoyl-SH$_2$K$_3$ formulation, that lacked disulphide bonding capacity, appeared to result in a lower level of activity after 7 days than formulations prepared with LPs that had disulphide bonding capacity (ie included a Cys residue). In the draining lymph nodes, the levels of activity were detectable but were 100-1000 fold lower than the levels observed in the gastrocnemius muscle tissue.

Example 4

Still further DNA complex particles were prepared, this time with messenger RNA (mRNA) as the nucleic acid cargo. In particular, mRNA with polyA at the 3' terminus was prepared by standard in vitro transcription from a plasmid including a cDNA encoding the CMV-nanoluciferase expression cassette from pNL1.1.CMV (Promega). The mRNA was capped at the 5' end, then formulated with PLGA-PEG and the stearoyl-CH$_2$K$_3$ lipopeptide, to produce negatively charged particles similar to those described in Example 3.

A dose equivalent to 10 µg mRNA was injected into the gastrocnemius muscle of C57 mice. The mice were euthanised after 24 hours to assay tissue for nanoluciferase expression as described above in Example 3.

Results

Figure 9:
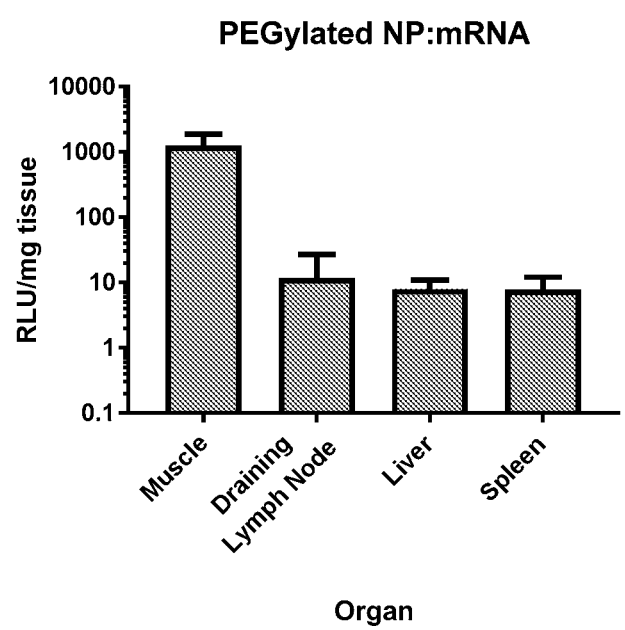
FIG. 9 provides graphical results showing the relative levels of expression of nanoluciferase in muscle, draining lymph node, liver and spleen after intramuscular injection of PLGA-PEG/LP/mRNA particles into c57 mice.

The results are shown in FIG. 9; expressed as relative luminescence intensity per mg of tissue. Luciferase expression was detected in muscle, draining lymph node, liver and spleen, but the level of expression in muscle was approximately 100 fold higher than that observed in the other tissues. The results confirm that agents according to the present disclosure can be used to condense and deliver mRNA to cells.

Throughout the specification and the claims that follow, unless the context requires otherwise, the words "comprise" and "include" and variations such as "comprising" and "including" will be understood to imply the inclusion of a stated integer or group of integers, but not the exclusion of any other integer or group of integers.

The reference to any prior art in this specification is not, and should not be taken as, an acknowledgement of any form of suggestion that such prior art forms part of the common general knowledge.

It will be appreciated by those skilled in the art that the agents and methods of the present disclosure are not restricted in their use to the particular application described. Neither are the present agents and methods restricted in their preferred embodiment with regard to the particular elements and/or features described or depicted herein. It will be appreciated that the agents and methods are not limited to the embodiment or embodiments disclosed, but are capable of numerous rearrangements, modifications and substitutions without departing from the scope of the present disclosure.

REFERENCES

1. Thomas C E et al., *Nat Rev Genet* 2003, 4:346-358.
2. Filion M C, Phillips N C, *Biochim Biophys Acta* 1997, 1329:345-356.
3. Harris T J et al., *Biomaterials* 2010, 31:998-1006.

4. Alexis F et al., *Mol Pharm* 5:505-515 (2008).
5. Bruun J et al., *Int J Nanomedicine* 10:5995-6008 (2015).
6. Tabernero J. et al., *Cancer Discov* 3:406-417 (2013).
7. Adami R C et al., *J Pharm Sci* 87:678-683 (1998).
8. Chen Q-R et al., *Nucleic Acids Res* 29:1334-1340 (2001).
9. McKenzie D L et al., *J Biol Chem* 275:9970-9977 (2000).
10. Ryu D-W et al., *J Cell Biochem* 112:1458-1466 (2011).
11. Tarwadi et al., *Bioconjugate Chem* 19:940-950 (2008).
12. Svitkin Y V et al., *Nucleic Acids Res* 45(10):6023-6036 (2017).
13. Boyle J S et al., *Int Immunol* 9:1897-1906 (1997).
14. Thompson B S et al., *J Leuk Biol* 78:1273-1280 (2005).
15. Ho J K et al., *Mol Ther Nucleic Acids* 5:e371 (2016).
16. White P J et al., *Vaccine* 26:6824-6831 (2008).
17. Atkins G J et al., *Exp Rev Mol Med* 10:e33 (2008).

The invention claimed is:

1. A non-viral nucleic acid delivery agent comprising a complex of:
   (i) a nucleic acid cargo for delivery to a cell;
   (ii) one or more cationic lipopeptide compound; and
   (iii) one or more polymeric charge-neutralising agent selected from the group consisting of poly-amino acid polymers, copolymers of polyethylene glycol (PEG) and a poly-amino acid polymer, and copolymers of poly(acrylic acid);
   wherein said complex is in the form of a particle with substantially neutral or negative surface charge, and the formation of said complex is conducted in the aqueous phase.

2. The delivery agent of claim 1, wherein the nucleic acid cargo is a DNA molecule which encodes a protein(s), oligopeptide(s) or peptide(s).

3. The delivery agent of claim 1, wherein the nucleic acid cargo is an mRNA molecule which encodes a protein(s), oligopeptide(s) or peptide(s).

4. The delivery agent of claim 1, wherein the nucleic acid cargo is a modRNA.

5. The delivery agent of claim 1, wherein the lipopeptide compound is of the general formula I:

(I) R-L-peptide wherein R is a linear or branched alkyl;
   L is a linker group; and
   the peptide is of any amino acid sequence comprising 2-15 amino acids, but with the proviso that at least two of the amino acids are independently selected from those with strongly basic/positively charged properties.

6. The delivery agent of claim 1, wherein the lipopeptide compound is of the general formula II:

(II) R—CO-peptide wherein
   R is $CH_3-(CH_2)_n-$, where n is an integer in the range of 11 to 21, and the peptide is of any amino acid sequence comprising 2-15 amino acids, but with the proviso that at least two of the amino acids are independently selected from those with strongly basic/positively charged properties.

7. The delivery agent of claim 5, wherein the peptide comprises 5-10 amino acids.

8. The delivery agent of claim 5, wherein at least two of the amino acids of the amino acid sequence are independently selected from lysine (Lys), arginine (Arg) and histidine (His).

9. The delivery agent of claim 6, wherein the lipopeptide compound is of the general formula: stearoyl-Cys-$X^1$-$X^2$-Lys-Lys-Lys (SEQ ID NO: 2), where $X^1$ and $X^2$ are any amino acids and may be the same or different.

10. The delivery agent of claim 6, wherein the lipopeptide compound is of the general formula: stearoyl-$X^0$-$X^1$-$X^2$-Lys-Lys-Lys, where $X^0$ is absent ($X^1$-$X^2$-Lys-Lys-Lys; SEQ ID NO:14) or any amino acid other than Cys ($X^0$-$X^1$-$X^2$-Lys-Lys-Lys; SEQ ID NO:3), and $X^1$ and $X^2$ are any amino acids other than Cys and may be the same or different.

11. The delivery agent of claim 10, wherein $X^0$ is Ser or Thr.

12. The delivery agent of claim 9, wherein $X^1$ and $X^2$ are independently selected from Ala, Arg and His.

13. The delivery agent of claim 10, wherein $X^1$ and $X^2$ are independently selected from Ala, Arg and His.

14. The delivery agent of claim 9, wherein $X^1$ and $X^2$ are His.

15. The delivery agent of claim 10, wherein $X^1$ and $X^2$ are His.

16. The delivery agent of claim 1, wherein the polymeric charge-neutralising agent(s) is selected from poly(L-glutamate)-PEG copolymers (PLGA-PEG) or copolymers of poly(acrylic acid).

17. The delivery agent of claim 16, wherein the polymeric charge-neutralising agent(s) is selected from block copolymers of poly(acrylic acid) and poly(hydroxypropyl methacrylamide) (polyHPMA), and block copolymers of poly (acrylic acid) and poly(2-hydroxyethyl methacrylamide) (polyHEMA).

18. The delivery agent of claim 1, wherein the particle shows a zeta potential (ZP) surface charge in the range of −2 to 2 mV or −40 to −5 mV.

19. A method of delivering a nucleic acid molecule to a cell of a subject, said method comprising the steps of:
   providing a non-viral nucleic acid delivery agent according to claim 1; and
   delivering the non-viral nucleic acid delivery agent to said cell of the subject.

20. The method of claim 19, wherein the non-viral nucleic acid delivery agent is delivered parentally to the subject.

21. A pharmaceutical composition comprising a non-viral delivery nucleic acid agent according to claim 1 in combination with a pharmaceutically acceptable carrier or excipient.

22. A method of producing a non-viral delivery nucleic acid agent according to claim 1, said method comprising:
   combining a nucleic acid cargo, one or more lipopeptide compound, and one or more polymeric charge-neutralising agent in the aqueous phase under conditions suitable for the formation of complexed particles.

* * * * *